US012788609B2

(12) United States Patent
Boyd

(10) Patent No.: US 12,788,609 B2
(45) Date of Patent: Nov. 10, 2026

(54) MULTILAYERED SUPPORT PAD INSERT FOR VENTRAL AND UMBILICAL HERNIA BINDER APPARATUS

(71) Applicant: Donald Boyd, Mattawa (CA)

(72) Inventor: Donald Boyd, Mattawa (CA)

( * ) Notice: Subject to any disclaimer, the term of this patent is extended or adjusted under 35 U.S.C. 154(b) by 0 days.

(21) Appl. No.: 18/942,692

(22) Filed: Nov. 9, 2024

(65) Prior Publication Data

US 2026/0115034 A1 Apr. 30, 2026

Related U.S. Application Data

(63) Continuation-in-part of application No. 17/079,490, filed on Oct. 25, 2020, now abandoned.

(60) Provisional application No. 62/925,974, filed on Oct. 25, 2019.

(51) Int. Cl.
*A61F 5/28* (2006.01)

(52) U.S. Cl.
CPC .................................... *A61F 5/28* (2013.01)

(58) Field of Classification Search
CPC ...... A61F 5/03; A61F 5/24; A61F 5/34; A61F 5/28; A61F 2/0063; A61F 5/026; A61F 5/022; A61F 5/028; A61F 5/30; A61F 5/0193; A61F 5/26; A61F 5/449; A61F 7/02; A61F 2005/0183; A61F 13/148; A61F 13/143; A61N 1/0456; A61N 1/0484; A41C 1/10; A41D 1/21; A41D 13/0525; A41D 13/1236; A44B 11/28
USPC ............. 602/75; 128/98.1, 96.1, 99.1, 104.1, 128/109.1, 121.1, 116.1, 122.1, 124.1, 128/108.1, 105.1
See application file for complete search history.

(56) References Cited

U.S. PATENT DOCUMENTS

| | | | | | |
|---|---|---|---|---|---|
| 1,475,921 | A * | 11/1923 | Redmond | A61F 5/24 | 450/150 |
| 1,916,298 | A * | 7/1933 | Brohman | A61F 5/03 | 128/96.1 |
| 5,885,230 | A * | 3/1999 | Cherry | A61F 5/03 | 600/595 |
| 2006/0253988 | A1 * | 11/2006 | Pearce | B29C 48/11 | 5/655.5 |
| 2014/0304900 | A1 * | 10/2014 | Sugano | A41D 13/0575 | 2/455 |
| 2015/0201685 | A1 * | 7/2015 | Brohmer | A41D 13/065 | 2/23 |
| 2021/0315288 | A1 * | 10/2021 | Gill | A41B 17/00 | |

FOREIGN PATENT DOCUMENTS

| | | | | |
|---|---|---|---|---|
| WO | WO-02074843 | A2 * | 9/2002 | B32B 27/32 |

* cited by examiner

*Primary Examiner* — Alireza Nia
*Assistant Examiner* — Michael Milo
(74) *Attorney, Agent, or Firm* — David W Barman

(57) ABSTRACT

A custom-made hernia support pad configured to be removably integrated on the inner side of a ventral and umbilical hernia binder apparatus. The support pad has a multilayered structure including a plurality of intermediate layers arranged in a stacked configuration and positioned inside a cover. At least two of the intermediate layers are composed of a polymeric material different from the material of the cover.

19 Claims, 19 Drawing Sheets

MULTILAYERED SUPPORT PAD INSERT FOR VENTRAL AND UMBILICAL HERNIA BINDER APPARATUS

CROSS-REFERENCE TO RELATED APPLICATIONS

This application is a continuation-in-part of U.S. patent application Ser. No. 17/079,490 filed Oct. 25, 2020, which claims the benefit of U.S. provisional patent application Ser. No. 62/925,974 filed Oct. 25, 2019, the disclosures of which are hereby incorporated by reference therein.

FIELD OF THE INVENTION

The present invention relates generally to a multilayered support pad insert for use with a ventral and umbilical hernia binder apparatus.

BACKGROUND OF THE INVENTION

A ventral hernia is a hernia that forms in the abdominal wall, along the midline, due to a weakness in the muscles that creates a gap. Typically, with a ventral hernia, abdominal tissues or a portion of the intestines protrude into the gap. Many cases of ventral hernias occur at the site of a previous surgical incision. This is because the incision weakens the abdominal muscles, putting them at an increased risk of injury due to obesity, strain, and/or aging. A ventral hernia can occur immediately following surgery or even years after the procedure.

The type of ventral hernia diagnosed is defined based on where the hernia forms: incisional hernia which is a ventral hernia that develops at a previous incision site; epigastric hernia which is a ventral hernia that develops within the abdominal area between the bottom of the breast bone and the belly button; and an umbilical hernia which is a ventral hernia that develops in the area surrounding the navel or belly button.

Ventral hernias typically require surgical intervention. The goal of ventral hernia surgery is to repair the gap in the abdominal wall and return the protruding tissues and organs to their natural position. A physician will determine the type of procedure performed after considering the severity of the hernia. There are two procedures that can be used to treat ventral hernias. An open ventral hernia repair is typically used for larger, more complex hernias. This surgery involves making one long incision near the hernia. In some cases, mesh made of animal tissue or a synthetic material may be used to hold the protruding tissues in place. Laparoscopic ventral hernia repair involves using a laparoscope, or a thin tube with a camera on the end, to guide the surgeon. During laparoscopic surgery, a surgeon will make three to four small incisions near the hernia. In some cases, mesh made of animal tissue or a synthetic material may be used to hold the protruding tissues in place. Laparoscopic repair is a minimally invasive technique that involves smaller incisions, a shorter time in the operating room, and faster recovery.

Recovery will vary for each patient, depending on the type of surgery performed and the overall health of the patient. Some patients may experience a low level of pain after an open repair procedure, while others may experience a high level of pain and discomfort, even after a minimally invasive laparoscopic procedure.

Intra-abdominal pressure is the pressure within the abdominal cavity. This pressure can increase due to various factors such as heavy lifting, obesity, pregnancy, chronic coughing, etc. When intra-abdominal pressure rises, it exerts force against the abdominal wall. If there is a pre-existing weak spot in the abdominal wall, such as a hernia, any activity or condition that raises intra-abdominal pressure can make the hernia worse, potentially causing it to enlarge or become more symptomatic. For example, lifting heavy objects or straining during bowel movements can increase pressure and push more of the abdominal contents into the hernial sac. However, intra-abdominal pressure can potentially be reduced or managed if it is diffused across a wider surface area. In some cases, wearing supportive garments such as abdominal binders or compression garments can help distribute pressure more evenly across the abdomen.

Accordingly, as part of the treatment and management of a ventral hernia, the patient may wear a belt or binder. The current belts, however, are primarily made as a one size for all type of device and does not account for the varying types and sizes of hernias. Furthermore, the current belts do not account for different stages in the patient's treatment—i.e., the preoperative stage and various stages throughout the patient's postoperative recovery. Accordingly, a device is needed to address the shortcomings and disadvantages of the prior art.

CN200954163 discloses an air-inflated pressuring hernia treating belt. The utility model discloses an air inflated pressurized hernia therapy belt for hernia auxiliary therapy medical. The model comprises a hernia therapy belt body with a retaining strap and a connecting strap positioned on the lower side and two sides, three medicine pocket nylon retainers are arranged in order on the inner side of the hernia therapy belt body. Three air bags communicate with the air inflation device are positioned on the place where is corresponding to the medicine pocket nylon retainer on the hernia therapy belt. The hernia therapy belt can be used for therapy on the direct hernia, tilted hernia, abdominal hernia, outer abdominal hernia and an umbilical hernia. Air inflation on the air bag adjusts the medicine pocket pressure at the hernia position, and has the advantages of balancing the hernia position to absorb effectively Chinese herbs and body comfort.

CN204072490 discloses an inflatable medical abdominal binder. The utility model relates to solving the problem of poor treatment effect of existing medical abdominal binders. The inflatable medical abdominal binder comprises a strip-shaped binder body, a plurality of internal air bags, a tube capsule air valve and a handheld inflation ball, wherein the two end heads of the binder body are provided with corresponding nylon hook-loop fasteners; a medicine placement bag is arranged on the inner side at a central position of the binder body. During use, the handheld inflation ball is used for inflating the plurality of internal air bags closely attached to the abdomen of a human body with pressure; the air bags are closely attached to the abdomen of the human body after being expanded; the abdomen is squeezed to be maintained in a compressed state once a person performs abdomen in slightly, the pressure is adjustable and the power exists continuously so as to facilitate postpartum uterine contraction, cut fixation after cesarean section, slimming, waist support and shape adjustment.

US20050182344 discloses a recovery belt apparatus. The device includes a pad portion attached to a first belt portion and a second belt portion. The device has a removable attaching means for attaching the first belt portion with the second belt portion. The pad portion is adapted to be placed over either a person's abdomen or thoracic area, and the removable attaching means adjusts pressure of the pad portion on either a person's abdomen or thoracic area.

Recovery belt apparatus includes pad portion coupled to a first belt portion on a first end and a second belt portion on a second end. Pad portion is of such a size to fit a surgical area of a person typical of surgical procedures, such as Cesarean section (C section), laparoscopic hiatal hernia, hernia, tummy tuck, hysterectomy, appendectomy, gall bladder surgery, thoracic surgery including lung or heart surgery.

CN205698235 discloses a pressurization binder for general surgical use. The utility model presses the belly and with the elastic strap. A cartridge bag can be filled with the traditional Chinese medicine, and an intermediate layer is filled with the gasbag. The air inlet on the gasbag, is provided with an end cap on the air inlet, the air inlet pressing the belly. The utility model discloses the beneficial effect through the control of the amount of aeration in the gasbag to adjust the elasticity between binder and the patient. The cartridge bag closely covers in the wound and Chinese herbal medicinal ingredient can promote wound healing in the cartridge bag to diminishing inflammation, shortening the patient's recovery time. The elastic strap is narrow in shape in width, and patient wears it thereby laminating the belly, prevent gliding by the elastic strap.

CN2082158 discloses a treatment binder for umbilical hernia. The utility model provides a baseband made by two pieces of pure cotton cloth that are folded and sewn, four elastic belts are sewn on the pure cotton cloth, bars with nylon hasps are sewn on the both ends of the baseband, sewing at the opposite side of a base strip, and a navel pad is also arranged at one end of the base strip. While the treatment binder for umbilical hernia is in use, the navel is pressed on the navel chakra of an infant, which is a wrapped circle for the treatment of umbilical hernia, and locked and combined by the bars with nylon hasps.

U.S. Pat. No. 9,220,585 discloses a hernia patch. The hernia patch supporting tissue in-growth conforms to a tissue wall upon surgical installation and fixation within a patient. The hernia patch can include a base and positioning straps. The base is formed of two layers that are affixed to each other around the perimeter of the patch, for example by stitching. A stabilizing washer is provided between the two layers, and the stitch is provided peripherally around the stabilizing washer, keeping the washer free-floating between the layers. The base, positioning straps, and stabilizing washer are formed of a structure that does not separate the layers of the implant or form a space in the form of a pocket, and promotes more uniform and confluent tissue incorporation or in-growth after implantation. The hernia patch may further include a hydrolysable bio-absorbable cross-linked coating of a fatty acid-based material, such as an omega-3 fatty acid based material.

US20070137642 discloses an infant stomach band to protect from injury. This band has particular usefulness in helping to prevent hernias in infants and preventing protruding belly buttons in infants. The band can have a especially useful applications for babies having colic. The cloth material is preferably stretchable and breathable while being a soft and comfortable material. Additional padding can be included beneath the cloth material and can be preferably positioned between a cloth material and elastic material to provide comfort to the infant. In a preferred embodiment the band compromises disposable materials substantially similar to the diaper materials used for infants' diapers. The band can include absorbent qualities as present in those in diapers while maintaining the predetermined geometrical shape to help prevent the hernia injuries and bulging belly button areas in infants.

U.S. Pat. No. 2,062,143 discloses an umbilical truss. The principal object of invention of the '143 patent is to provide an improved, more efficient and comfortable truss for the relief of conditions arising from umbilical hernia. A further object of the '143 patent is to provide a truss of the type mentioned in which a balance is achieved between the bearing portion of the pad and the rear portion of the belt, thus increasing the efficiency, as well as the comfort of the truss in use. A further object of the '143 patent is to provide in an umbilical truss a pad having a bearing head which is adapted to rotate upon a supporting stem, the head thus being adapted to remain constantly at the point of rupture during all conditions of movement by the user.

WO2018144456 discloses a hernia belt. A hernia belt may include a digitally knitted support belt and a two-part fastening system. The two-part fastening system may include a first part and a second part, in which the second part includes a plurality of fastener strips arranged spaced apart from each other. The digitally knitted support belt may include mesh stitch layouts for providing breathability and support.

U.S. Pat. No. 5,195,948 discloses an adjustable back support device. A back support device is disclosed comprising a belt structure designed to fit substantially around the waist of a user. An inflatable air bladder is attached inside the belt structure so that it is positioned adjacent to the lower back when the back support device is worn. Several embodiments of elastic strap members are disclosed which are attached between the air bladder and belt structure. The strap members enable the user to adjust the direction of force exerted by the air bladder on the lower back and help to pull the air bladder around the waist. A manual air plump with two-way valve is positioned inside the belt structure near one end, which enables the user to selectively adjust the amount of air in the air bladder while the back support device is worn. Using the above device, a method of providing back support is also disclosed.

All cited documents are herein incorporated by reference in their entirety.

None of the above cited documents, alone or in combination satisfy the need for a hernia binder that has multi-purpose insert pockets which efficiently and effectively provides abdominal and lumbar support and while not permitting bulging of the ventral hernia.

SUMMARY OF THE INVENTION

It is an object of the present invention to provide a ventral hernia binder with a patient-specific, custom-made support pad insert.

In accordance with one or more embodiments, there is provided a custom-made hernia support pad that is configured to be removably integrated on the inner side of a ventral and umbilical hernia binder apparatus, described below. The support pad has a multilayered structure including and outer cover and a plurality of intermediate layers. The outer cover includes a front panel and a back panel, each having a perimeter, and one or more side flanges connecting the perimeter of the front panel to the perimeter of the back panel to form an enclosed structure. The enclosed structure defines an interior cavity. The plurality of intermediate layers is arranged in a stacked configuration and has a perimeter. The plurality of intermediate layers are configured to be positioned in the interior cavity between the front and back panels. At least two of the intermediates layers are composed of a polymeric material different from the materials of the front and back panels.

In accordance with an embodiment, each of the front panel and the back panel is comprised of an aromatic polyamide, an aliphatic polyamide, or a lignocellulose fiber, or a combination thereof. The front panel may have a composition different from the back panel.

In accordance with an embodiment, the plurality of intermediate layers includes a shock-absorbing high-density foam layer proximate or adjacent to the front panel.

In accordance with an embodiment, the plurality of intermediate layers includes a shock-absorbing high-density foam layer proximate or adjacent to the back panel.

In accordance with an embodiment, the plurality of intermediate layers includes a (first) shock-absorbing high-density foam layer proximate or adjacent to the front panel and another (a second) shock-absorbing high-density foam layer proximate or adjacent to the back panel.

In accordance with an embodiment, the plurality of intermediate layers includes a compressible elastomer layer proximate to the front panel.

In accordance with an embodiment, the plurality of intermediate layers includes a compressible (first) elastomer layer proximate or adjacent to the back panel.

In accordance with an embodiment, the plurality of intermediate layers includes a compressible elastomer layer proximate or adjacent to the high-density foam layer.

In accordance with an embodiment, the plurality of intermediate layers includes a resilient (a second) elastomer layer.

In accordance with an embodiment, the plurality of intermediate layers includes a polyethylene layer.

In accordance with an embodiment, wherein the plurality of intermediate layers includes another compressible (a third) elastomer layer.

In accordance with an embodiment, the polyethylene layer is positioned between the (first) high-density foam layer and the another (second) high-density foam layer.

In accordance with an embodiment, the resilient (second) elastomer layer is positioned between the (first) high-density foam layer and the another (second) high-density foam layer.

In accordance with an embodiment, the support pad includes a base layer positioned between the plurality of intermediate layers and the back panel. The base layer extends laterally beyond the perimeter of the plurality of intermediate layers.

In accordance with an embodiment, the compressible (first) elastomer layer is proximate or adjacent to the back panel and the polyethylene layer is positioned between the high-density foam layer and the compressible (first) elastomer layer.

In accordance with an embodiment, the another compressible (third) elastomer layer is positioned between the high-density foam layer and the polyethylene layer.

In accordance with an embodiment, the compressible (first) elastomer layer is proximate or adjacent to the back panel and the resilient (second) elastomer layer is positioned between the high-density foam layer and the compressible (first) elastomer layer.

In accordance with an embodiment, the polyethylene layer is positioned adjacent or proximate to the resilient (second) elastomer layer.

In accordance with an embodiment, the another (third) compressible elastomer layer is positioned between the high-density foam layer and the resilient (second) elastomer layer.

In accordance with an embodiment, the another (third) compressible elastomer layer is positioned adjacent or proximate to the high-density foam layer.

In accordance with an embodiment, the interior cavity is accessible via a zipper assembly.

In accordance with an embodiment, the ventral hernia binder apparatus comprises a binder belt having an inner and outer surface; one or more means of fastening said binder on position on a patient; and a pouch positioned on said inner surface of said binder belt, said pouch being sized and positioned to correspond to a location of said ventral hernia, said pouch further being sized to accommodate a support pad insert.

As used herein, "removably integrated" refers to being insertable and removable from a pocket or pouch on the inner side of the binder apparatus, or secured by other means, such as a with complementary first and second fastening components. For example, the first fastening component may be on one side of the support pad and the second fastening component may be on one side of the binder apparatus. When the two fastening components are engaged, the support pad is secured to the binder belt.

In accordance with an embodiment, there is provided a method of preventing the occurrence of a ventral hernia in a patient in need of such therapy using a ventral hernia binder apparatus having one more fasteners and one or more internal pouches, said method comprising the steps of: positioning said ventral hernia binder apparatus at an appropriate position to cover said ventral hernia; placing an insert in one or more of said one or more internal pouches; and securing said one more fasteners to hold said ventral hernia binder apparatus at said appropriate position on said patient.

In accordance with an embodiment, there is provided a method of preventing the recurrence of a ventral hernia in a patient in need of such therapy using a ventral hernia binder apparatus having one more fasteners and one or more internal pouches, said method comprising the steps of: positioning said ventral hernia binder apparatus at an appropriate position to cover said ventral hernia; placing an insert in one or more of said one or more internal pouches; and securing said one more fasteners to hold said ventral hernia binder apparatus at said appropriate position on said patient.

The advantages and features of the present invention will become better understood with reference to the following more detailed description and claims taken in conjunction with the accompanying drawings in which like elements are identified with like symbols.

To easily identify the discussion of any particular element or act, the most significant digit or digits in a reference number refer to the figure number in which that element is first introduced.

BRIEF DESCRIPTION OF DRAWINGS

To easily identify the discussion of any particular element or act, the most significant digit or digits in a reference number refer to the figure number in which that element is first introduced.

DETAILED DESCRIPTION OF THE EMBODIMENTS

Figure 1:
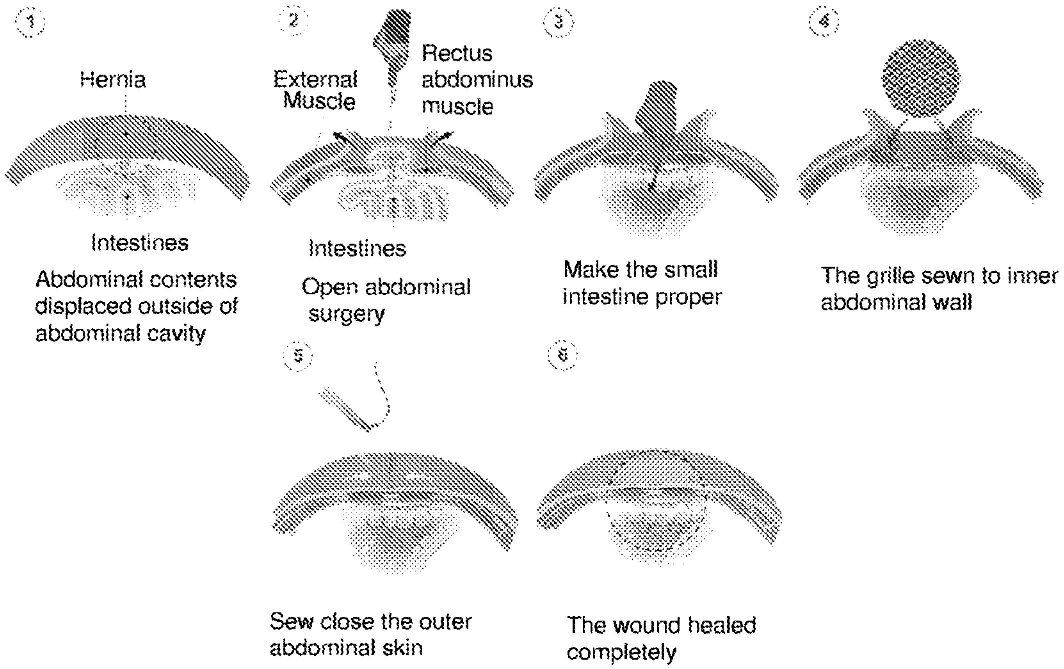
FIG. 1 illustrates the formation and subsequent repair of a ventral hernia.

The various embodiments of the present disclosure will hereinafter be described in conjunction with the appended drawings, wherein like designations denote like elements.

Devices and methods for carrying out the invention are presented in terms of embodiments depicted within the figures. However, the invention is not limited to the described embodiments, and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present disclosure, and the configurations shall be shown and described for purposes of clarity and disclosure and not by way of limitation of scope.

A hernia is the bulging of the intestine or fat that pushes its way through a weakened area in the abdominal wall. There are more than one million hernia surgeries a year in the US, they may be located in the groin area, and are called inguinal hernias, or in the abdominal area, and are called ventral hernias. Men and women, even children can be affected, but men are the majority of hernia patients.

In view of the disadvantages inherent in the known art, the present invention provides a novel patient-specific, custom-made support pad insert for use with a hernia binder. The present invention addresses the aforementioned shortcomings and disadvantages of the prior art by efficiently and effectively providing abdominal and lumbar support while not permitting bulging of the ventral hernia. The abdominal prosthetic, as described herein, can be worn to prevent hernias from developing, or can be worn after surgery, with the patient-specific, custom-made support pad insert, to protect the herniated surgical site.

Hernias are typically repaired by either laparoscopic or open surgery. With laparoscopic repair, a small video camera is inserted through incisions in the abdominal wall. The cavity is inflated with carbon dioxide and the surgeon can pull the hernia back into place securing it with mesh and staples or tacks and glue. For open surgery, an incision is made in the abdomen and the hernia is pushed back into place and the abdominal muscle wall is stitched together, if the muscle is healthy, or by sewing in mesh patches if the area is weak.

In the field of major abdominal wall reconstruction, recurrence is the most important complication. In order to reduce recurrence rates, meshes are used as reinforcement of augmentation or bridging of large abdominal wall defects. Numerous meshes, including metal, polyester and biodegradable fabrics are available worldwide, differing in material, pore size, weight, tensile strength, elasticity and biocompatibility.

To help prevent hernia distention post-op and rupturing of the implanted mesh, a binder is often worn post-surgery by patients. However, known hernia binder belts often do not prevent the internal organs from pushing against the mesh and causing a bulging or distension when performing everyday activities such as picking up a heavy object or bending down. The hernia belt as described herein is configured to accommodate patient-specific, custom-made support pad inserts that provide additional support to the herniated site pre and post-op. By increasing the internal abdominal pressure and support in the region of weakened abdominal tissue, the various embodiments of the present disclosure assist patients with preoperative issues, post op-physiotherapy and everyday activities.

In an embodiment, the custom-made support pad insert is placed between a hernia and a binder in order to prevent bulging of the hernia through a weakness in the abdominal wall muscles. The support pad may be constructed in different sizes and shapes to conform to the patient's size, the specific hernia and other factors. The support pad may also be constructed from various materials to accommodate these factors. The support pad may be created from a mold of the specific patient who will utilize the present invention.

The support pad is therefore custom-made and is constructed in different sizes and shapes to conform to the patient's size, the specific hernia and other factors. The support pad may be secured to the binders through various fasteners, including a hook and mesh fastener, sometimes known as Velcro.

In one embodiment, the patient-facing side of the support pad is shaped to conform to the shape of the patient's abdomen around and including the hernia site. In one embodiment, the outside-facing side of the support pad is further shaped to the imitate the musculature and shape of the patient's abdomen (see FIGS. 3A-3B).

In one embodiment, the hernia binder may be configured to be lightweight and flexible, which is typically made from a combination of breathable, stretchable, and durable materials like nylon, spandex, a soft elastic mesh fabric, or other materials that exhibit similar properties, or a combination thereof. The flexibility of the binder ensures that it conforms closely to the body, adapting to the contours of the wearer's abdomen, as well as to the shape of the support pad. By doing so, the binder holds the support pad against the hernia site in a snug, yet comfortable manner, ensuring it remains in position, while minimizing the appearance of a protruding object beneath the wearer's clothing.

The hernia binder may also include an airbag or bladder to provide additional support to the patient, including lumbar support and abdominal wall support. In some embodiments, the hernia binder may also include airbag or bladder to provide additional support to the patient, including lumbar support and abdominal wall support. An air bag nozzle may be located on the front side of the apparatus to allow for easy patient access to control the amount of air in the bladder.

In some embodiments, the binder of the present invention may include one or more flexible, but resistant, bands or rods that are embedded within the binder and/or support pad or support pad pouch. These bands will provide additional support to a patient in order to keep the patient in a more vertical position in order to assist with the daily movement of the patient.

The support bands or rods are multifunctional and can be inserted in many different positions in the binder. The support rods or bands may be used in the region of the tissue that is at risk of becoming herniated or, when a hernia has been repaired, they may be positioned to support and prevent recurrence. The support rods or bands may be used in the lumbar region to support the musculature in the lower back and relieve stress and pain.

In some embodiments, the support rods or bands that are installed in the anterior of the binder cooperate with the support rods or bands that are installed in the posterior of binder. In this embodiment, the anterior rods or bands protect and support the ventral musculature when the patient is performing everyday tasks, such as bending forward. In this embodiment, the posterior rods or bands similarly protect and support the ventral musculature, and function in an opposing and off-setting manner to the anterior rods or bands, to assist in returning the body to an upright position.

In alternative embodiments of the hernia binder, the apparatus may take the form of a vest or a full upper body garment and may include groin of thigh support elements. Support rods may be incorporated into pouches or sleeves in various positions within the binder, for example, some patients having neck and upper spinal lateral cord issues in the C5-C7 region may benefit from additional support to the pectoralis major and minor muscles, via the lateral and medial pectoral nerves, as well as the coracobrachialis, brachialis and biceps brachii, via the musculocutaneous nerve.

The support rods or bands may be fabricated from various metals or plastics, typically including steel, stainless steel, copper or any medical grade plastic having the appropriate strength. The rods or bands may be coated in a protective material such as foam, rubber or fabric. In instances, where the hernia repair has resulted in removal of large quantities of musculature, the custom-made support pad may contain one of more support rods or bands to hold the support pad in shape and provide additional support to the weakened musculature in the herniated region.

The features of embodiments which are believed to be novel are particularly pointed out in the specification. Embodiments of the present disclosure now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the present disclosure to those skilled in the art.

Figure 10:
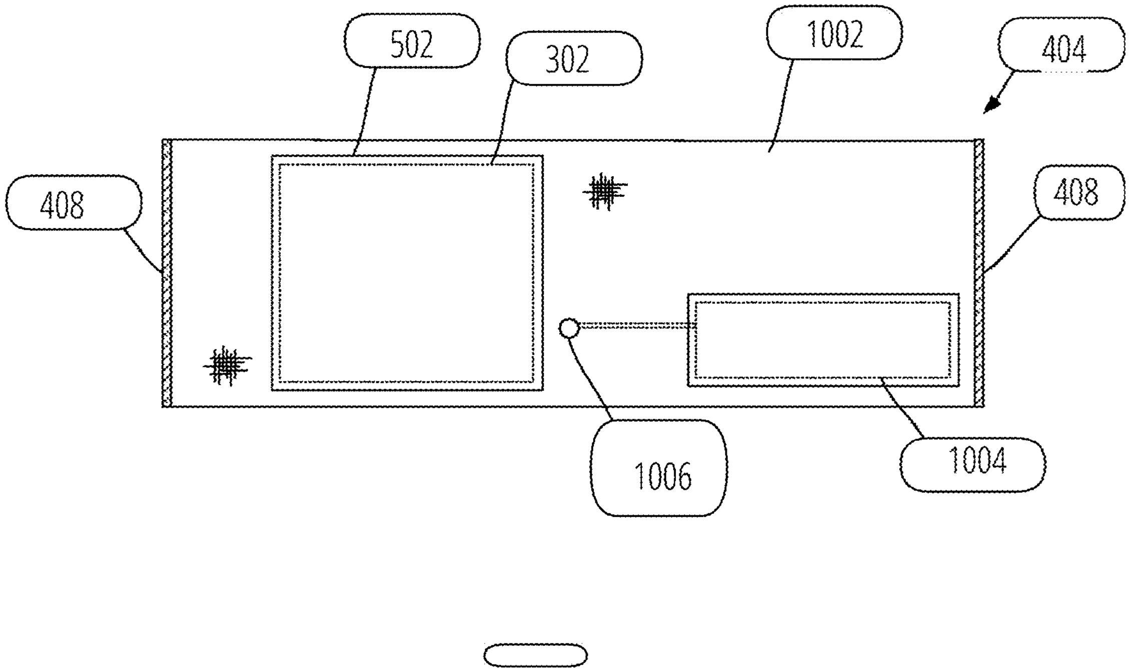
FIG. 10 illustrates a rear view of an additional embodiment of the present disclosure including lumbar support provided by an air bag.
Figure 11:
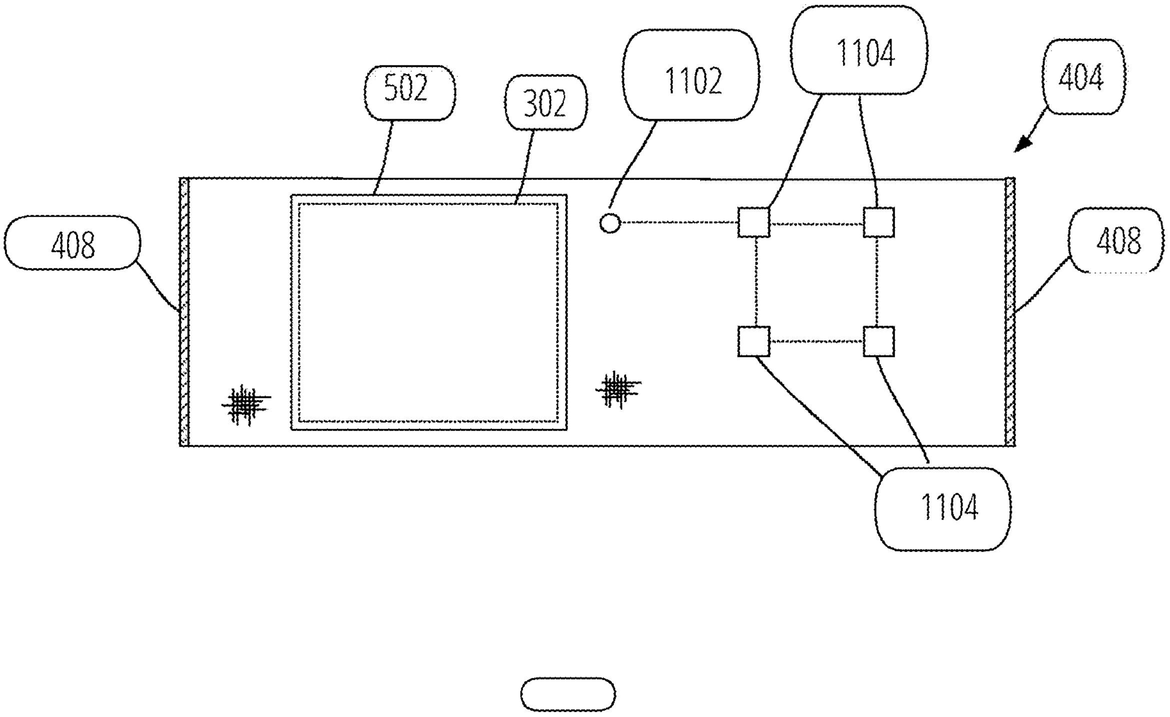
FIG. 11 illustrates a rear view of an additional embodiment of the present disclosure including TENS technology.
Figure 12:
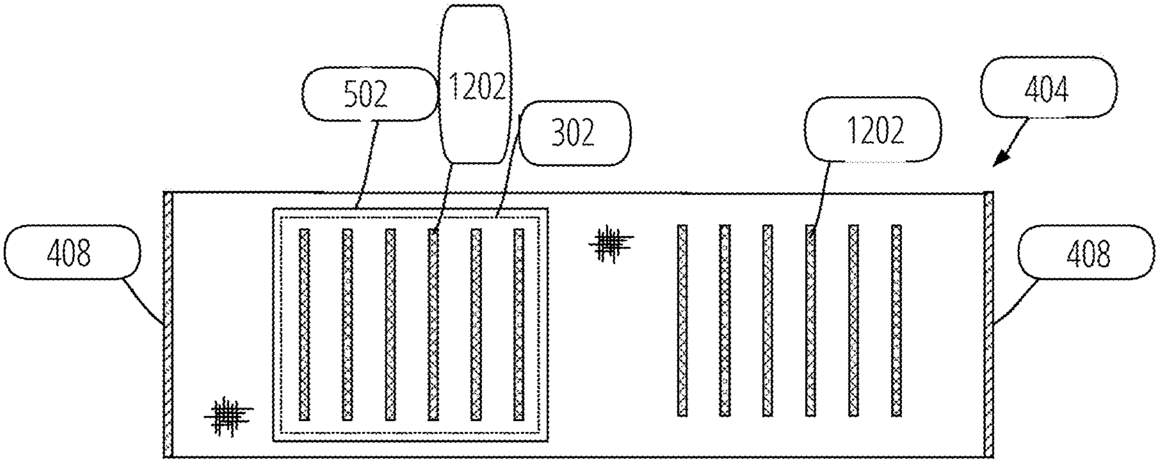
FIG. 12 illustrates a rear view of yet an additional embodiment of the present disclosure including support bands.
Figure 13:
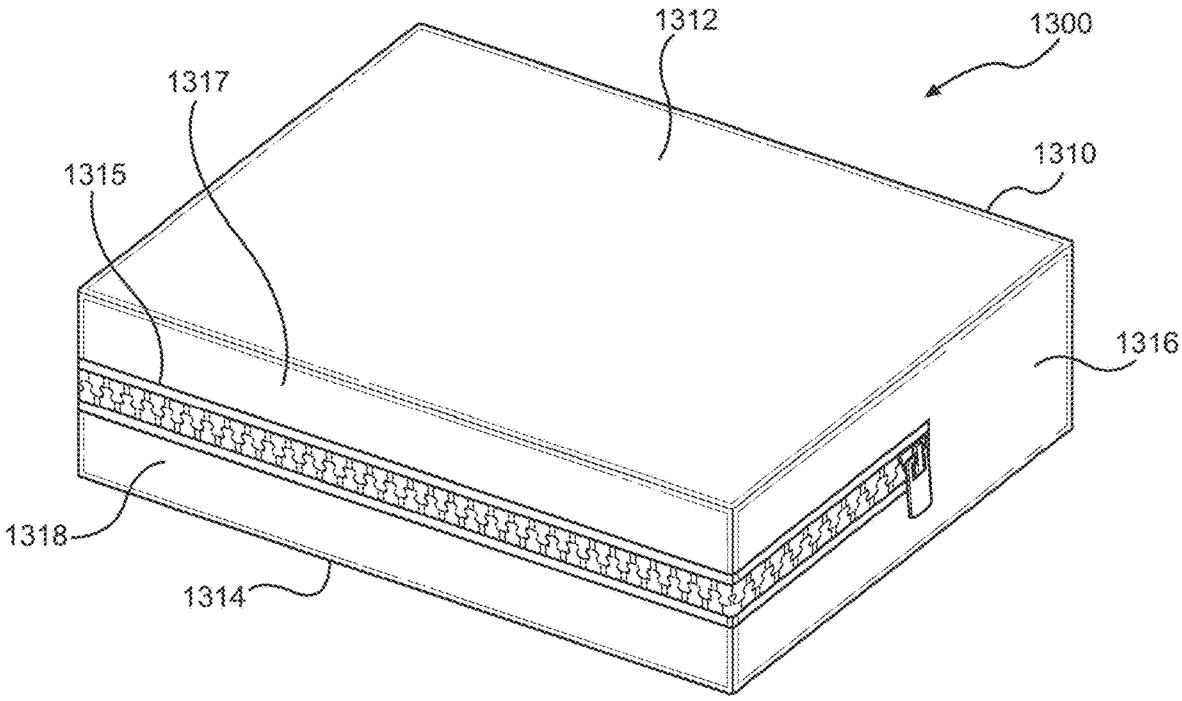
FIG. 13 illustrates an isometric view of a multilayered support pad insert that is zipped closed in accordance with one or more embodiments of the present disclosure.

Referring now to the drawings, there is shown in FIGS. 1-2 the anatomy and correction of a ventral hernia. FIG. 3 shows a custom-made support pad in accordance with an embodiment of the present disclosure. FIGS. 4-9 show various different embodiments of the binder apparatus. FIGS. 10-12 show various different additional features of the ventral hernia binder of the present disclosure. FIGS. 13-18 shows various views of multilayered support pad inserts in accordance with a plurality of embodiments of the present disclosure. FIGS. 19A-22B shows cross-section views of various multilayered support pad inserts in accordance with a plurality of embodiments of the present disclosure.

FIG. 1 illustrates the various stages of ventral hernia repair. FIG. 1.1 shows a hernia formed under the skin due to the intestines or abdominal contents being displaced outside the abdominal cavity. FIG. 1.2 illustrates the exposure of herniated tissue during an open abdominal surgery. FIG. 1.3 shows the herniated tissue, including fat and/or intestines, being re-inserted back into the abdominal cavity. FIG. 1.4 indicates the placement of a grille or mesh patch being implanted on the inner surface of the abdominal wall. FIG. 1.5 shows the surgical repair of the initial incision wound. FIG. 1.6 shows a healed hernia.

Figure 2A:
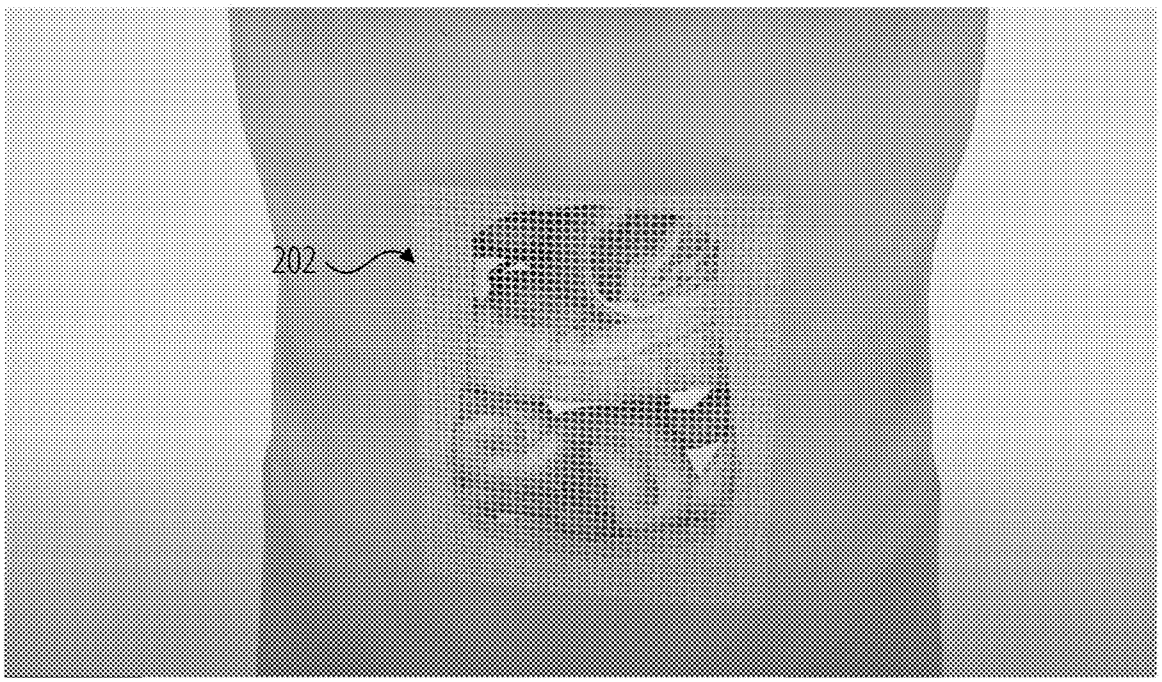
FIGS. 2*a* and 2*b* illustrates placement of implanted mesh after a ventral hernia repair and subsequent 3D imaging of repaired hernia site.

FIG. 2A illustrates a pictorial view of the abdomen and internal organs. After a hernia has been repaired, a layer of implanted mesh 202 is secured in place on the inner surface of the abdominal wall (not shown).

Figure 2B:
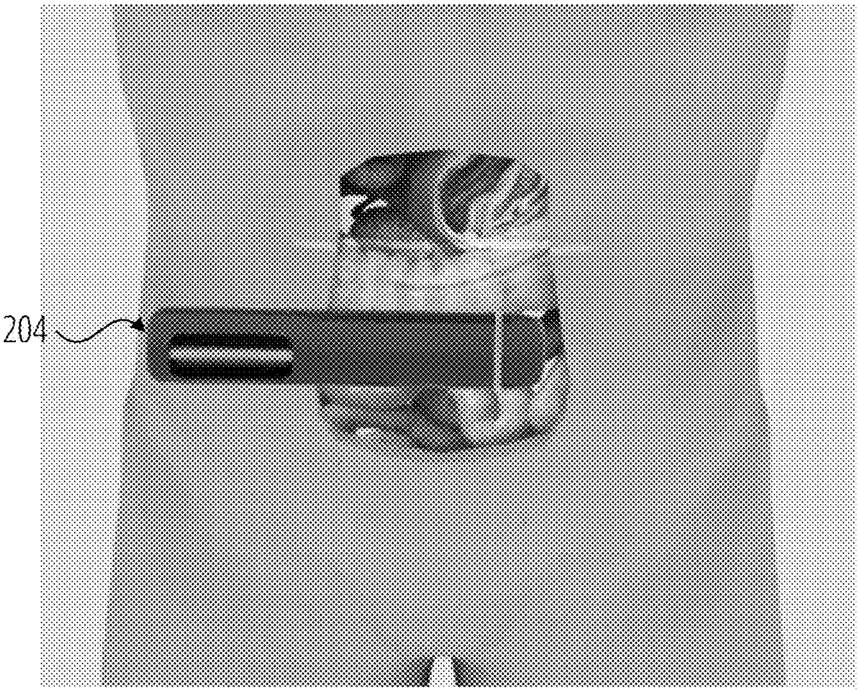

FIG. 2B illustrates a method of producing a 3D image, in this embodiment by use of a 3D measuring device 204 such as a 3D-laser. Other techniques known in the medical filed would include, but are not limited to, plaster casting, ultrasound, MRI's or CAT scans.

Figure 3A:
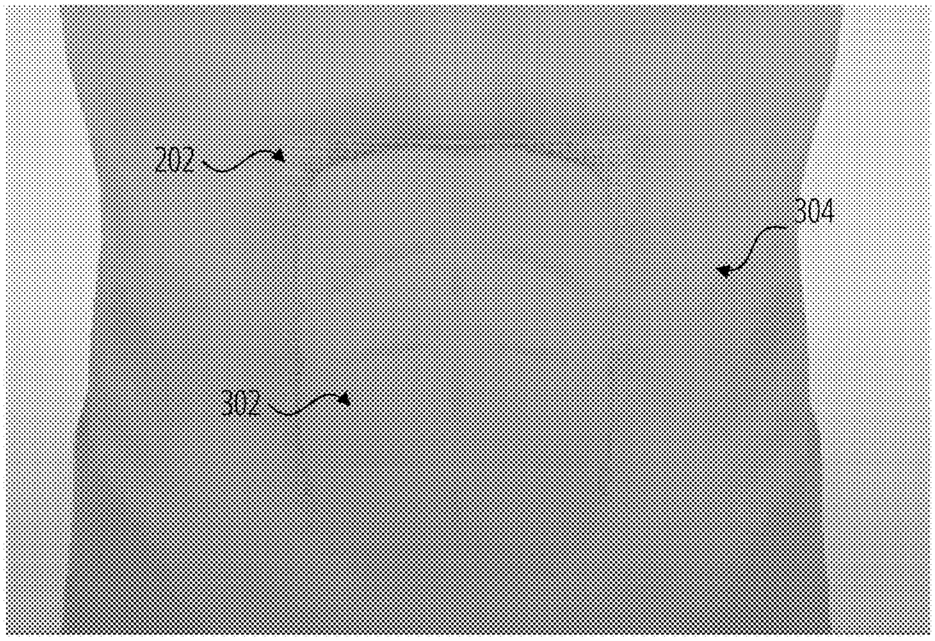
FIGS. 3*a* and 3*b* illustrates views of aspects of embodiments of the subject matter in accordance with one embodiment of the present disclosure.

FIG. 3A shows the positioning of a custom-made support pad 302 that has been produced in accordance with one of the known techniques outlined above. The custom-made support pad 302 is positioned over the approximate area of the weakened area of the abdomen 304 that has the implanted mesh 202 attached beneath it.

Figure 3B:
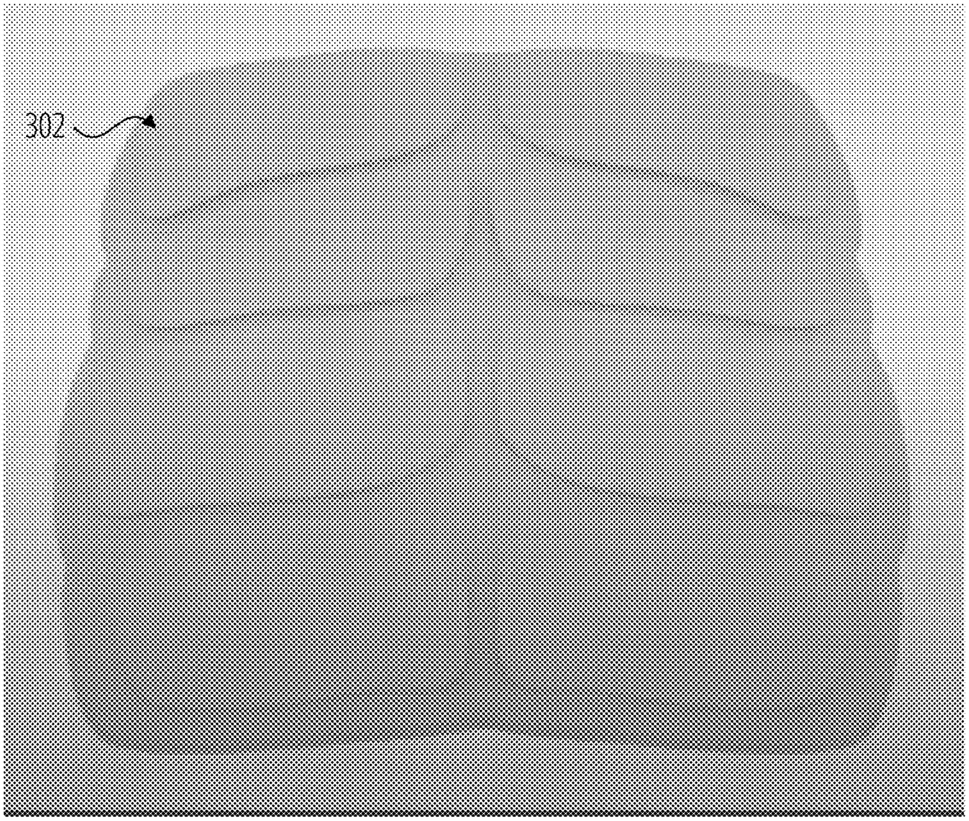

FIG. 3B shows a close-up representation of a custom-made support pad 302. The custom support pads 302 can be fabricated from flexible or more rigid material, and they are washable.

Figure 4:
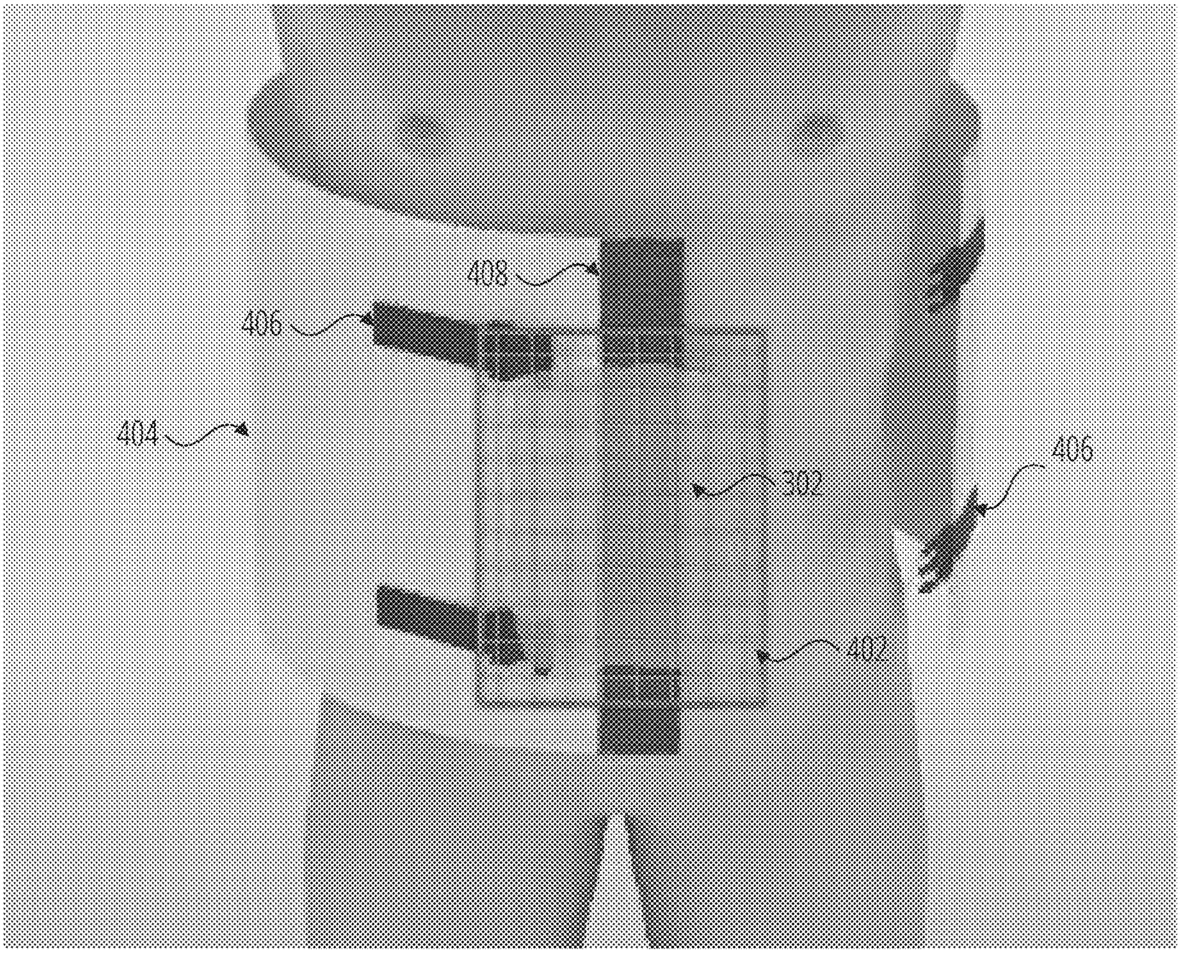
FIG. 4 illustrates positioning of an abdominal binder in accordance with one embodiment of the present disclosure.

FIG. 4 shows a diagrammatic representation of mesh 402 and it relative positioning within the abdominal cavity. The position of the custom-made support pad 302, over the implanted mesh 202 can be seen. A binder 404 of an embodiment of the present disclosure can be seen being sized and fitted to the patient. The binder 404 is secured in place by way of first securement means 408 and first securement means 408.

Figure 5A:
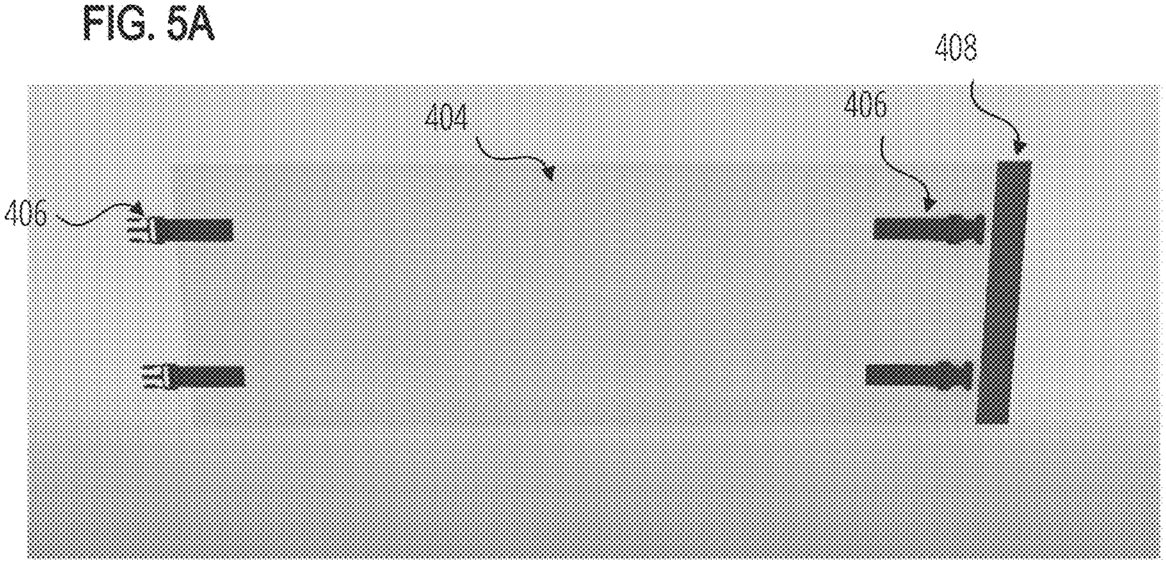
FIGS. 5A and 5B illustrates front and back views of an abdominal binder, with insert pouch, in accordance with one embodiment of the present disclosure.

FIG. 5A shows a front or outer side view of a binder 404 in accordance with an embodiment of the present disclosure. The first securement means 408 and second securement means 406 can be seen.

Figure 5B:
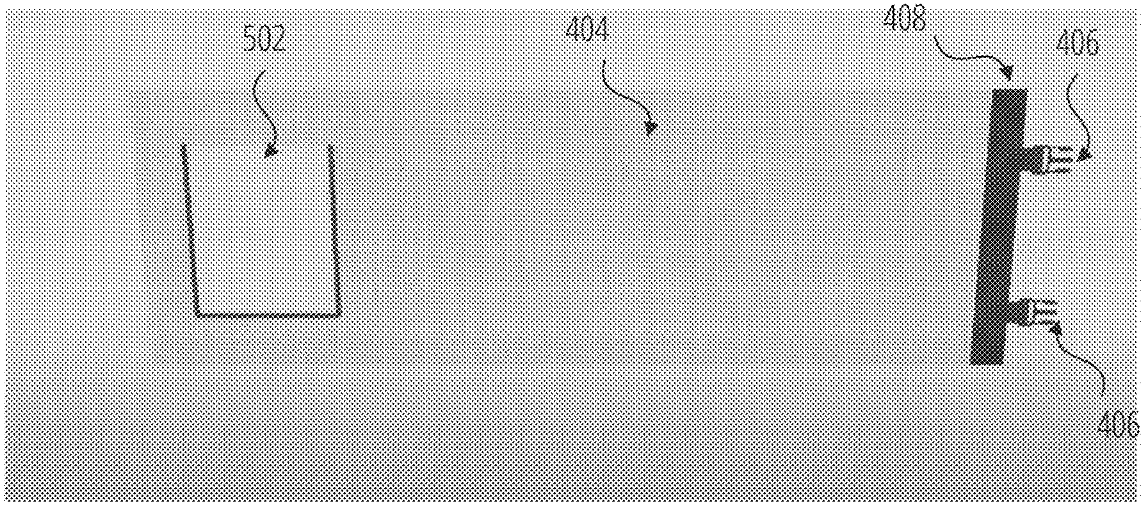

FIG. 5B shows a rear or inner side view of a binder 404 in accordance with an embodiment of the present disclosure. The custom positioned insert pouch 502 can be seen to correspond with the position of the implanted mesh 202 (not shown).

Figure 6:
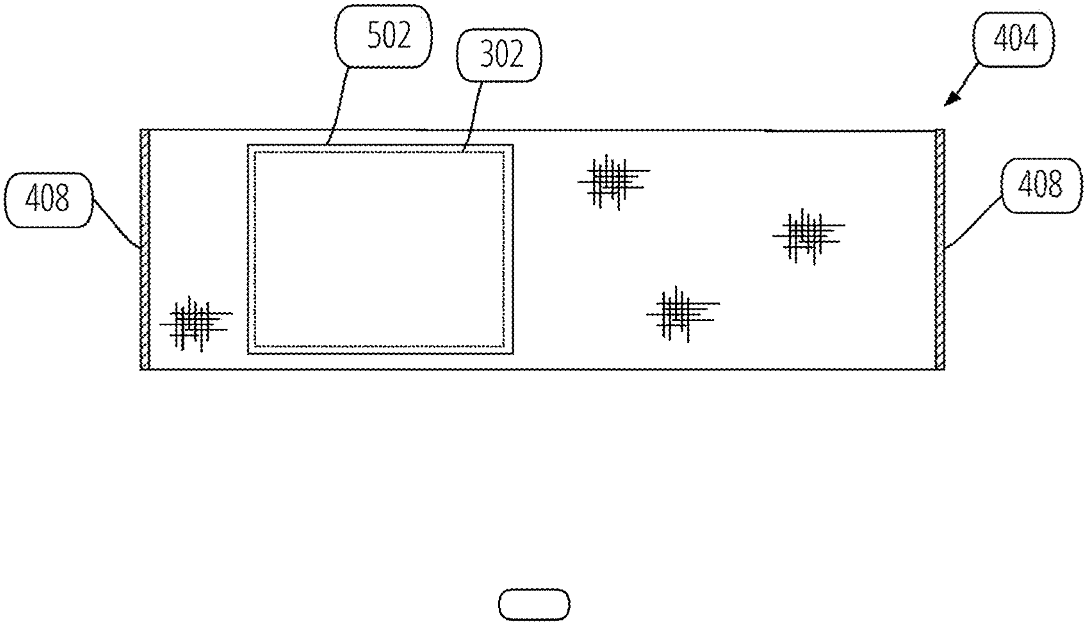
FIG. 6 illustrates a diagrammatic front view of an embodiment of the present disclosure.

FIG. 6 shows a rear or inner side view of an embodiment of the binder 404. In this embodiment, the first securement means 408 are fabricated from a strip of Velcro®. Again, the support pad pouch 502 containing the custom-made support pad 302 can be seen.

Figure 7:
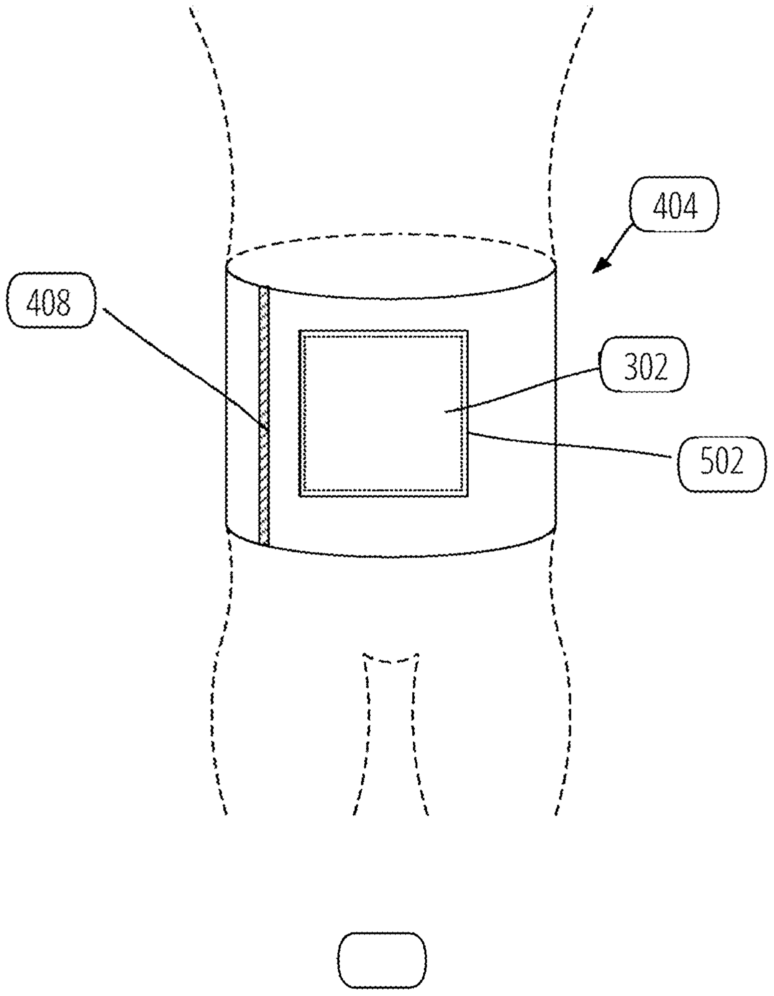
FIG. 7 illustrates a perspective front view of an additional embodiment in use.

FIG. 7 shows the relative positioning of a binder 404 of an embodiment of the present disclosure when worn in the abdominal region of the body. The inner positioning of the support pad pouch 502 and custom-made support pad 302 are indicated.

Figure 8:
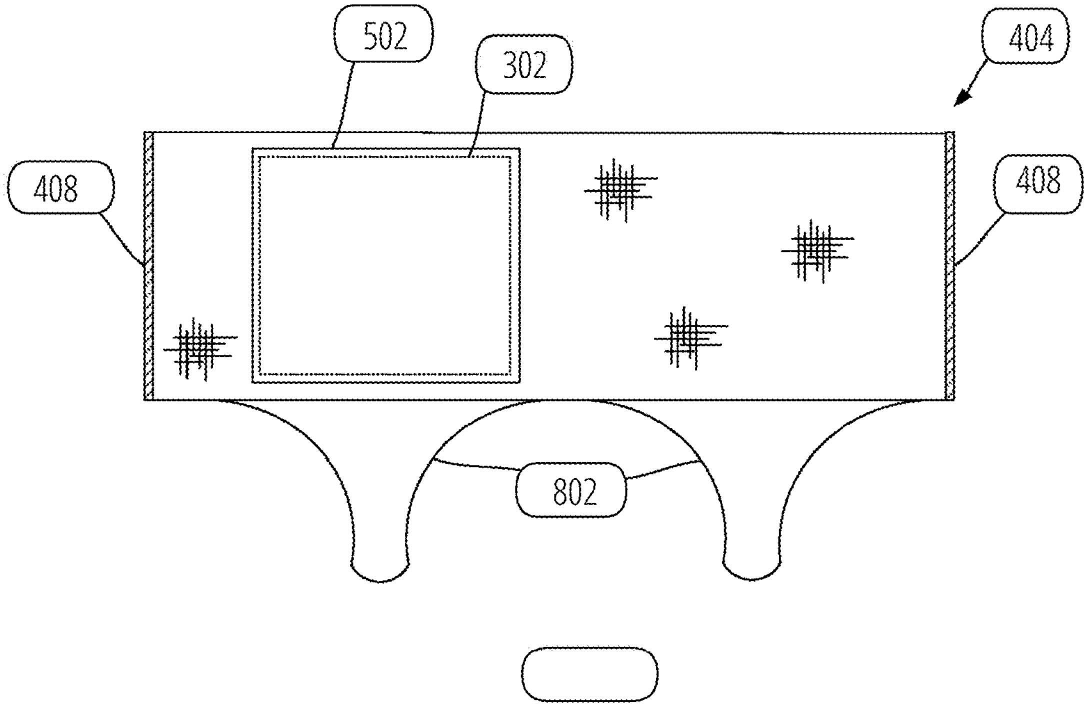
FIG. 8 illustrates an aspect of the subject matter in accordance with an alternative embodiment of the present disclosure.

FIG. 8 illustrates an alternative embodiment of a binder of the present disclosure. The binder 404 comprises a first securement means 408, and optional first securement means 408 (not shown) and the inner support pad pouch 502 and custom-made support pad 302. However, this embodiment of the binder additionally has a groin support member 802.

Figure 9:
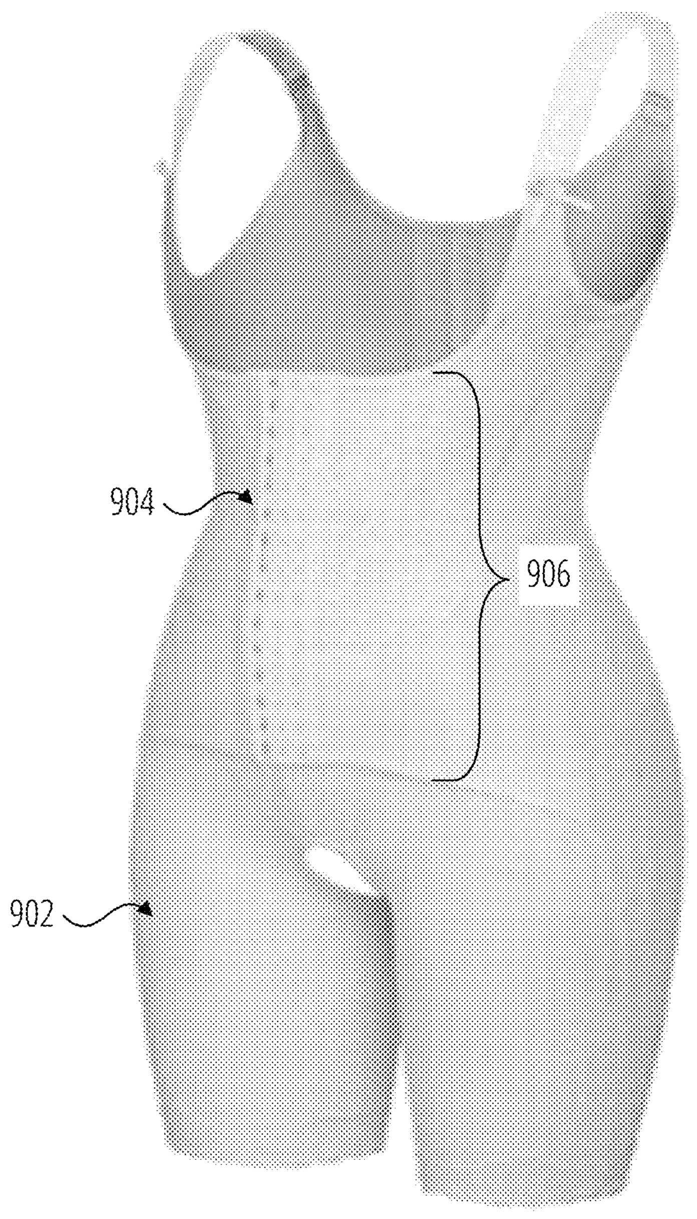
FIG. 9 illustrates an aspect of the subject matter in accordance with an alternative embodiment of the present disclosure.

FIG. 9 illustrates full body compression outfit 904 comprising an extended binder 906 which may be suitable for a multiple hernia patient. The extended binder 906 or full body suit 904 is custom fitted to the patient and may comprise thigh members 902 that extend around upper portions of the legs.

FIG. 10 shows an embodiment of a hernia binder 404 essentially as illustrated in FIG. 6, however the hernia binder 404 shown in this fig also features an air bag/bladder 1004 in communication with an air bag/bladder nozzle 1006. The positioning of the air bag/bladder 1004 is such that it will provide lumbar support. In alternative embodiments of the present disclosure, the air bag/bladder 1004 can be positioned in the region of the herniated tissue in order to provide additional support to the custom support pad 302.

FIG. 11 shows an embodiment of a hernia binder 404 essentially as illustrated in FIG. 6, however the hernia binder 404 shown in this figure also features a transcutaneous electrical nerve stimulation (TENS) treatment device. The TENS device comprises one or more TENS unit pads 1104 and a TENS unit switch 1102 to activate the TENS device. These components comprise standard TENS electrical unit electrode pads, wiring, controller hardware, batteries and other standard TENS unit components. This embodiment of the present disclosure may be configured to comprise a TENS unit pouch (not shown) to safely and securely retain the TENS device in an appropriate position within the binder 404.

Transcutaneous electrical nerve stimulation (TENS) therapy involves the use of low-voltage electric currents to treat pain. A small device delivers the current at or near nerves. TENS therapy blocks or changes perception of pain. A TENS unit consists of a battery-powered device that delivers electrical impulses through electrodes placed on the surface of the skin. The electrodes are placed at or near nerves where the pain is located or at trigger points.

FIG. 12 illustrates shows an embodiment of a hernia binder 404 essentially as illustrated in FIG. 6, however the hernia binder 404 shown in this fig also features a number of support bands 1202. In the embodiment as illustrated, some of the support bands 1202 are situated in the region of the herniated tissue and some are located in the lumbar region of the back to provide additional support and relieve back pain.

FIGS. 13-22B illustrate, in accordance with a plurality of embodiments, multilayered (laminated) custom-made support pad inserts that are configured to be removably integrated with a ventral hernia binder apparatus, such as the binder apparatus described above. In particular, the support pad may be custom-made so as to be shaped to correspond to at least a ventral hernia. The composition of each support pad is selected specific to the needs of the patient. The multilayered structure includes an outer cover (1310) having a front (or first) panel (1312), a back (or second) panel (1314), and a plurality of intermediate (or core) layers (1330). Front and back panels (1312, 1314) are arranged on opposing sides of the multilayered structure, with seam flanges (1316*a*, 1316*b*) and zipper flanges (1317, 1319) overlaying and enclosing the sides of the plurality of intermediate layers (1330). Intermediate layers (1330) are arranged in a stacked configuration and positioned between the front and back panels (1312, 1314). The thickness of each layer is customized according to the needs of the particular patient, as will be described below.

FIGS. 13-18 illustrate, in accordance with one or more embodiments, a multilayered support pad 1300 having an outer cover 1310 and a plurality of intermediate layers 1330. (For brevity, the plurality of intermediate layers 1330 may be referred to as "the intermediate layers 1330".) Cover 1310 includes a front panel 1312 and a back panel 1314, which are joined together along their respective edges to form inner cavity 1324 for housing the intermediate layers 1330 (see FIGS. 16-18). Cover 1310 features a zipper assembly 1315 that allows for access to inner cavity 1324. For the purpose of this disclosure, the term "zipper assembly" refers to any fastening mechanism that features interlocking teeth, tracks, coils, or other elements attached to a base material, tape, or fabric layer, which is configured to be joined to the edges of the respective top and bottom panels (1312, 1314) of cover 1310. Zipper assembly 1315 includes a slider mechanism that, when moved along the length of the interlocking elements, selectively opens or closes the enclosure by engaging or disengaging the interlocking elements. This may include the zipper elements shown in the drawings or variations that provide a similar function of releasable fastening.

Figure 17:
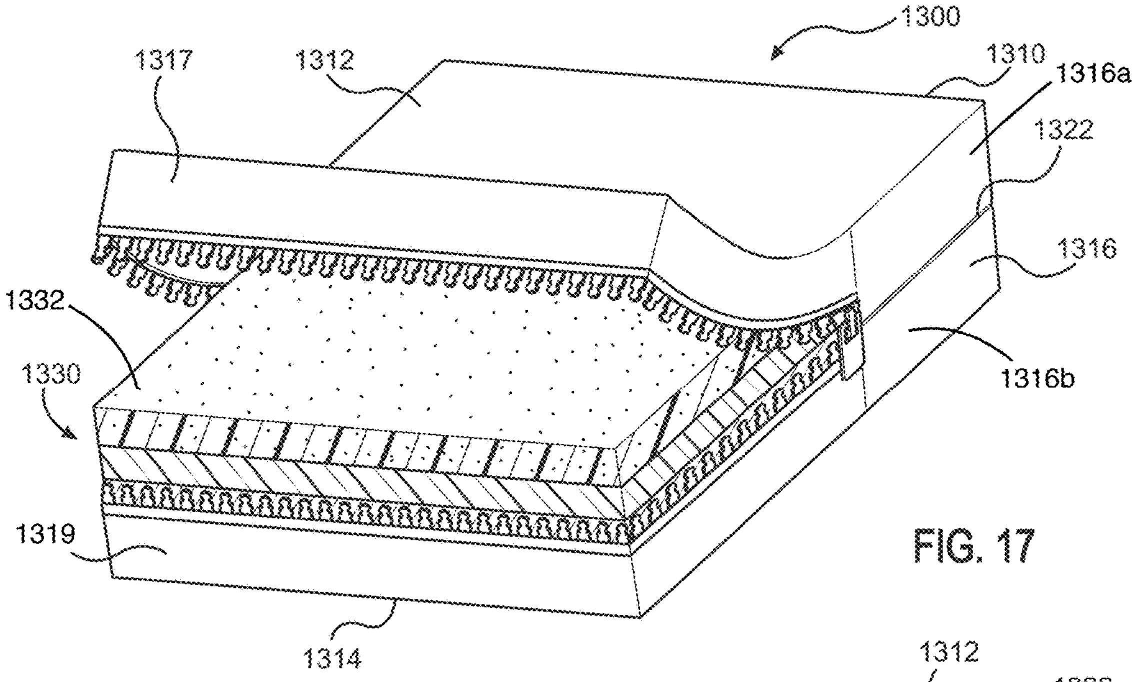
FIG. 17 is an isometric view of a multilayered support pad, such as shown in FIG. 13, having an outer cover unzipped and partially peeled back, exposing inner features, in accordance with one or more embodiments of the present disclosure.
Figure 18:
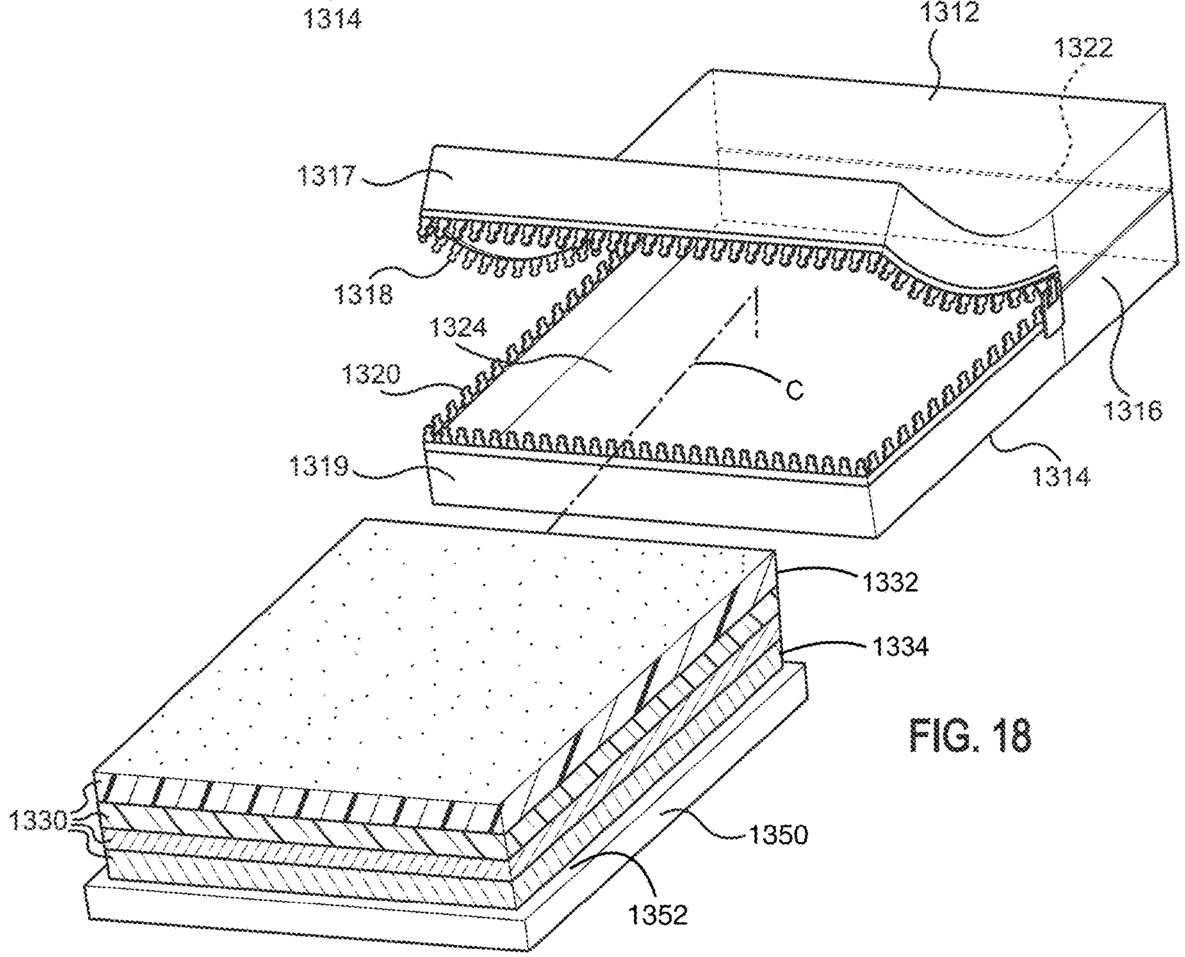
FIG. 18 is an isometric view of a multilayered support pad, such as shown in FIG. 17, having an outer cover unzipped and partially peeled back, with the inner contents removed so as to expose the inner cavity of the outer cover, and having an arrow indicating the position for inserting the inner contents, in accordance with one or more embodiments of the present disclosure.

Zipper assembly 1315, also referred to interchangeably as zipper closure, zippered mouth or zipper portion, includes a first (or front) zipper flange 1317 having a first (or front) set of interlocking teeth 1318 and a second (or back) zipper flange 1319 having a second (or back) set of interlocking teeth 1320. As illustrated in FIGS. 17-18, each zipper flange (1317, 1319) extends perpendicularly from the outer peripheral edge of the inner surface of the respective front panel 1312 and back panel 1314. Together, these flanges form an enclosure for accommodating a zipper mechanism. The zipper flanges (1317, 1319) may be integrally formed with their respective front and back panels (1312, 1314) or may be fixedly attached to them along a seam.

Figure 14:
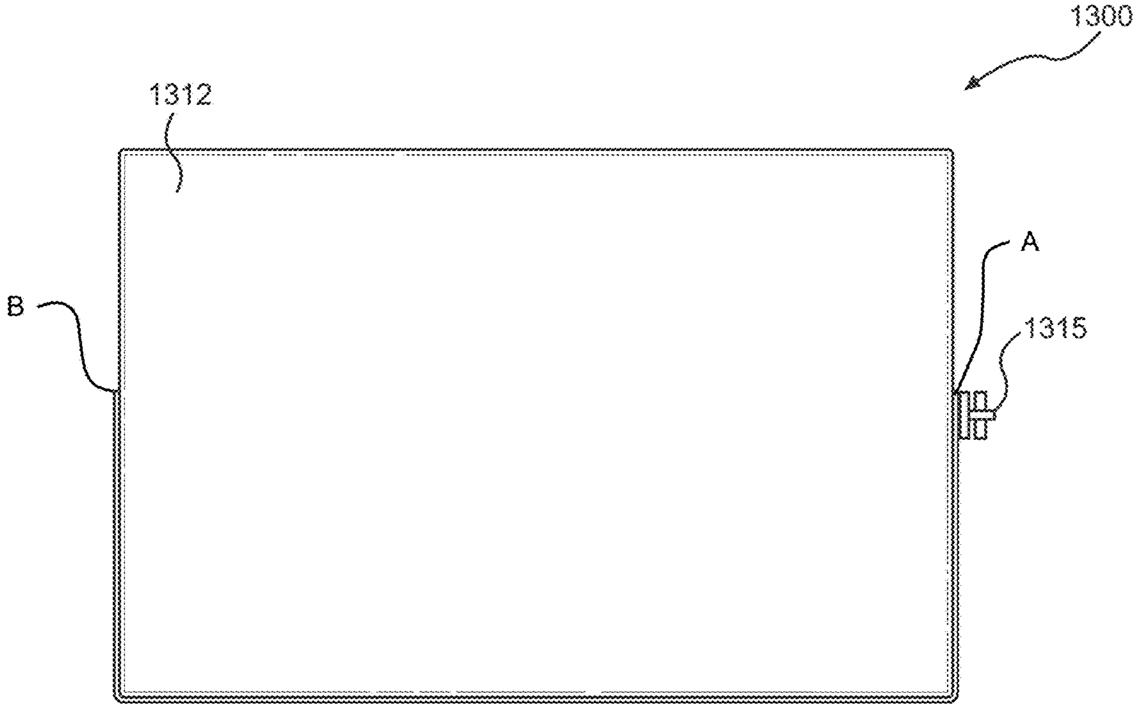
FIG. 14 illustrates a top view of the support pad shown in FIG. 13.
Figure 15:
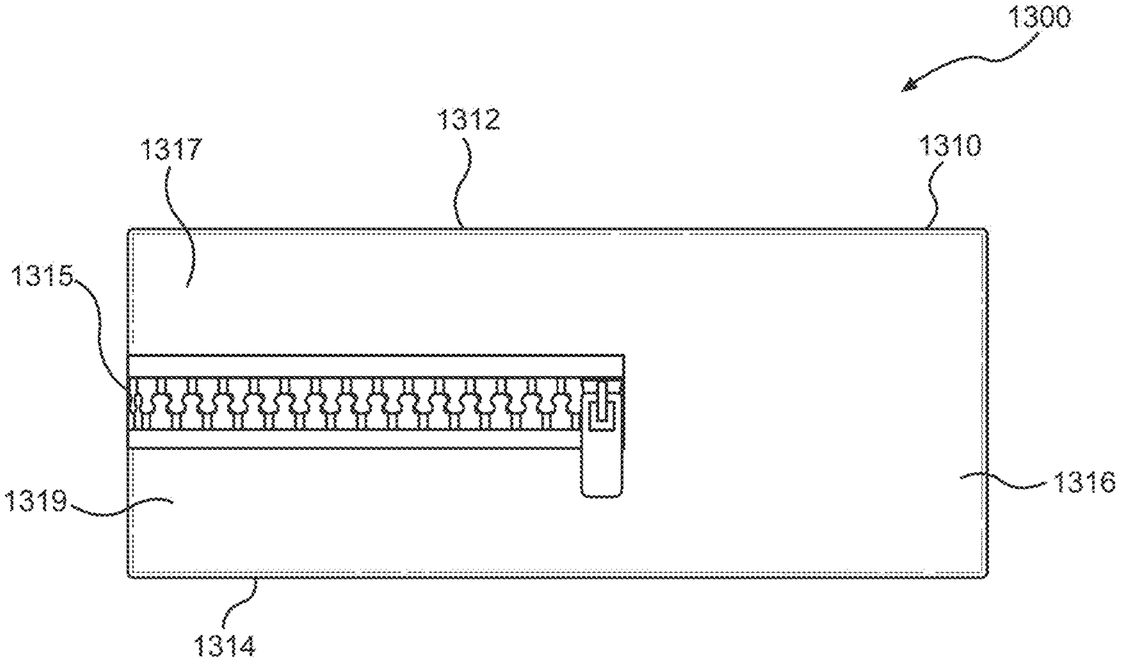
FIG. 15 illustrates a side view of the support pad shown in FIG. 13.

Zipper assembly 1315 is shown extending approximately 190 degrees along the perimeter of cover 1310, beginning at point A and terminating at point B (see FIG. 14). However, it should be understood that the zipper assembly may extend along different lengths of the perimeter as desired. In various embodiments, zipper assembly (1315) may extend from about 90 degrees to about 270 degrees along the perimeter, or any suitable length within this range, depending on the specific requirements of the application.

The remaining length of the perimeter of cover 1310, which may be referred to interchangeably as fixed side panel 1316, is a seamed portion that extends continuously from point A to point B opposite the zipper portion 1315 (see FIGS. 14 and 17-18). Fixed side panel 1316 includes a first (of front) seam flange 1316*a* and a second (or back) seam flange 1316*b*, which are joined along seam 1322 (see FIGS. 17-18). Seam 1322 provides structural integrity along the midline of fixed side panel 1316. Each of the first and second seam flanges (1316*a*, 1316*b*) extend perpendicularly from the outer peripheral edge of the inner surface of the respective front panel 1312 and back panel 1314. The seam flanges (1316*a*, 1316*b*) may be integrally formed with their respective front and back panels (1312, 1314) or may be fixedly attached to them along respective seams.

Figure 16:
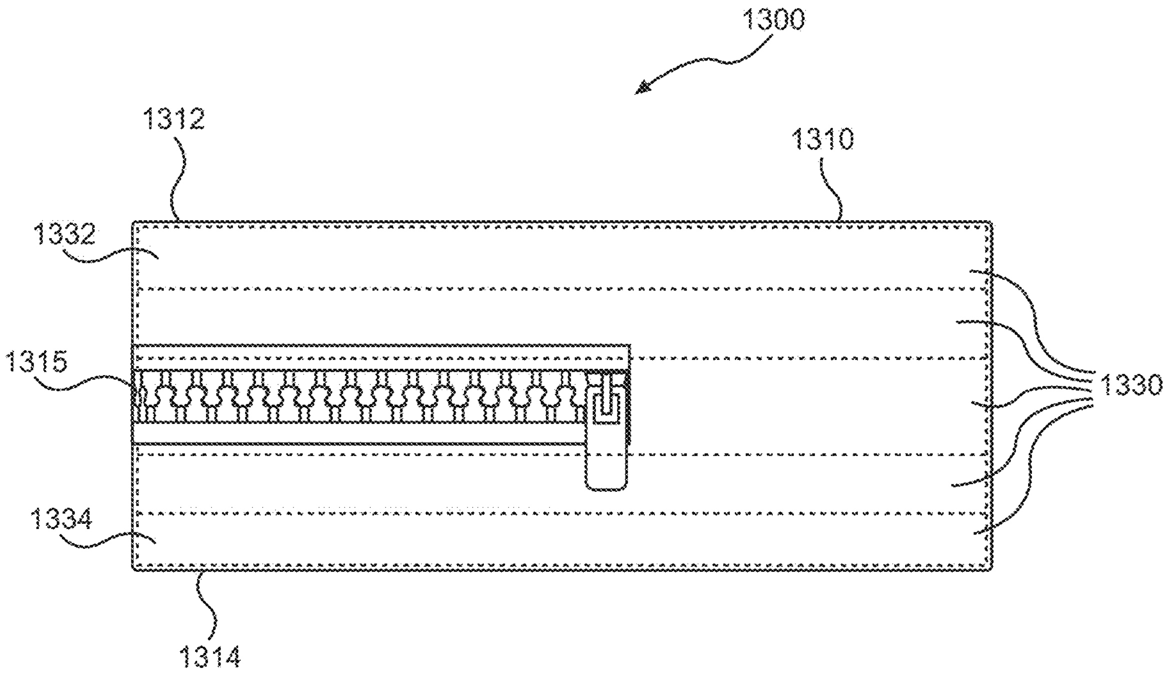
FIG. 16 a side view in partial section of the support pad of FIG. 15, showing interior features in phantom lines, with outer features also depicted, in accordance with one or more embodiments of the present disclosure.

In one or more embodiments, such as shown in FIGS. 16-17, the inner contents (i.e., the intermediate layers 1330) of cover 1310 completely or nearly completely fill the inner cavity (1324), such that the intermediate layers 1330 are in contact with the entire interior surface of cover 1310. For example, in FIG. 16, a first intermediate layer 1332 (e.g., a polyurethane high-density foam layer) is in contact with the inner surface of front panel 1312, while a second intermediate layer 1334 (e.g., a first elastomer layer) is in contact with the inner surface of back panel 1314. Due to the custom-made nature of support pads 1300, inner cavity 1324 is configured to fully contain and conform to the shape and dimensions of the intermediate layers 1330 without any unfilled space remaining. In alternate embodiments, some unfilled space may remain, as desired, such as to accommodate the optional insertion of one or more additional components, or for other reasons.

In one or more embodiments, such as shown in FIG. 18, inner cavity 1324 is configured to accommodate the intermediate layers 1330 having an additional base layer 1350. In this configuration, the intermediate layers 1330 as a whole resembles a top-hat having two rectangular, planar sections stacked vertically: an upper top section ("crown") being the intermediate layers 1330 and a lower section ("base" or "brim") being the base layer 1350. The upper and lower sections may also be referred to as respective first and second sections. Intermediate layers 1330 (crown) and the base layer 1350 (brim) each have a rectangular profile in an isometric view, with the base layer 1350 (brim) being uniformly larger than the intermediate layers 1330 (crown) in all directions along the same horizontal axis. The Intermediate layers 1330 (crown) are centrally aligned over the base layer 1350 (brim), such that the central axis of the intermediate layers 1330 (crown) aligns with the central axis of base layer 1350 (brim). Base layer 1350 (brim) has horizontal dimensions extending from about one inch to about two inches beyond the perimeter of the intermediate layers 1330 (crown) on all sides (i.e., in all four lateral directions), forming a uniform margin 1352 around the intermediate layers 1330 (crown's) footprint. In these embodiments, the base layer 1350 (brim) portion of the inner contents fills the entire cavity 1324 along both horizontal axes, contacting the interior surface on all sides of second zippered side panel 1319, while the intermediate layers 1330 (crown) portion of the inner contents only partially fills cavity 1324. In this configuration, there may be unfilled spaces or gaps within inner cavity 1324 where certain contents—i.e., the intermediate layers 1330 (crown)—do not reach the interior walls of first and second zippered side panels (1317, 1319).

The margin portion 1352 of base layer 1350 has been described as extending from about one inch to about two inches beyond the perimeter of the intermediate layers 1330 on all lateral sides. However, the margin portion 1352 may be further extended as desired (e.g., two and one-half inches, three inches, four inches).

In alternate embodiments from the embodiments described above in connection with FIG. 18, cover 1310 is configured having a top-hat shape including a flared base section to accommodate the above-described margin 1352 of the base layer 1350. In this configuration, cover 1310 further includes a first vertical wall extending upward from back panel 1314, defining the lower boundary of inner cavity 1324, an inward-facing ledge extending inward from the top of the first vertical wall, and a second vertical wall extending from the inner rim of the inward-facing ledge. The upper edge of the second vertical wall terminates with the second set of interlocking teeth (1320). In this configuration, when the inner contents (1330 and 1350 combined) have been inserted into cavity 1324, the inward-facing ledge of cover 1310 folds over the above-described margin 1352 of base layer 1350 in order that, when cover 1310 is closed, its walls conform to the top-hat shape and dimensions of the combination of the intermediate layers 1330 and base layer 1350, resulting in limited or no unfilled space.

Although cover 1310 is shown in the illustrated embodiments as having a rectangular shape, other suitable shapes may be adopted. Such shapes may include regular geometric shapes or irregular geometric shapes. Regular geometric shapes include, but are not limited to, other polygons (e.g., hexagon, octagon, rectangles, squares, trapezoids, triangles) and ovals (e.g., circle and ellipse). An irregular shape may include, but is not limited to, a shape that compliments the shape of the support pad. A non-limiting example of such an irregular shape is represented by support pad 302 as depicted in FIG. 3B.

FIG. 18 further illustrates that cavity 1324 is exposed when zipper closure 1315 is opened and one or both of first and second zipper flanges (1317, 1319) is peeled back. This configuration allows for removal or insertion of the inner contents (1330 or the combination of 1330 and 1350) of support pad 1300. The inner contents are inserted in the direction of arrow "C" into inner cavity 1324.

Embodiments have been described, in connection with FIGS. 13-18, depicting a cover 1310 that opens along its midline on its side (1317, 1319) perpendicular to, and in between, front and back panels (1312, 1314). In an alternate embodiment, a zipper closure is disposed along the perimeter of the top panel (1312). In this configuration, the zipper extends substantially around the entire perimeter of the top panel (1312), allowing the top panel (1312) to lift up and provide access to the interior cavity (1324) of cover (1310). This alternate arrangement facilitates a full, wide opening for the top panel (1312), which enhances the accessibility of the inner contents within the cover (1310). In a similar, alternate embodiment, the zipper closure is disposed along the perimeter of the bottom panel (1314). While these alternate embodiments are not depicted in the drawings, they are fully contemplated as part of the present disclosure.

As shown in FIGS. 19A-22B, in accordance with one or more embodiments, front panel 1312 is arranged on the left-side of support pad 1300 and back panel 1314 is arranged on the right-side of support pad 1300. When support pad 1300 is properly inserted into inner support pad pouch 502 of hernia binder 404 (described above), the left side of support pad 1300 is the outer-facing (or outside-facing) while the right-side is the patient-facing side or inner-facing side (or inside-facing). The patient-facing side is the side proximate or adjacent to the hernia site, which is the side typically requiring the most cushioning support.

It should be understood that the absence of base layer 1350 in FIGS. 19A-22*b* does not imply that this feature is necessarily absent from the embodiments depicted therein. Rather, base layer 1350, as illustrated in FIGS. 13-18, may be present in some embodiments corresponding to FIGS. 19A-22B, while it may be omitted in other embodiments. Accordingly, the presence or absence of base layer 1350 in the illustrations is intended to demonstrate various possible configurations and is not limiting.

It should be understood that although FIGS. 13-18 illustrate front and back panels (1312, 1314) of outer cover 1310 as being separate from respective adjoining layers of the inner contents (e.g., layers 1332 and 1350 in the example depicted in FIG. 18), the absence of visible separation in FIGS. 19A-22B does not imply that front and back panels (1312, 1314) are necessarily fused or attached to the adjoining features in those embodiments. Rather, this distinction is provided to demonstrate possible configurations, and the embodiments depicted in FIGS. 19A-22B may include front and back panels (1312, 1314) as either separate from, or integrally connected to, adjacent features, depending on the intended implementation.

In accordance with some of the embodiments described above in connection with FIGS. 13-18, outer cover 1310 is separate from the intermediate layers 1330. In these embodiments, cover 1310 has a pouch-like configuration having cavity 1324 into which the intermediate layers 1330 are inserted, or from which they are removed. Cover 1310 may be machine washable. The inner contents may include base layer 1350. Cover 1310 is shown having a zipper closure 1315, although other closure mechanisms may be utilized, such as, but not limited to, button fasteners, clip fasteners, snap fasteners, hook and loop fasteners, and the like.

In one or more alternate embodiments, outer cover 1310 is integrally formed with the intermediate layers 1330 such that front panel 1312 is a first outer layer and back panel 1314 is a second outer layer. In this configuration, continuous side panel 1316 may extend along the entire length of the perimeter of cover 1310. Thus, FIGS. 19A-22B may also be understood as supporting, in the alternative, a support pad 1300 whose cover 1310 is integrally formed with its inner contents, which requires disassembly of the seam or other fixed closures in order to insert or remove the inner contents.

In one more embodiments, the front and back panels (1312, 1314) are composed of different materials. The panels (1312, 1314) may be sown together along a seam (refer to seam 1322 in FIGS. 17-18) or otherwise joined at least partially along their shaped perimeter.

In one more embodiments, the front and back panels (1312, 1314) are composed of the same material. Front and back panels (1312, 1314) may be integrally formed as a single continuous layer having a pouch-like or clam-like shape or may be separate panels that are sown together along a seam (similar to seam 1322 shown in FIGS. 17-18), or otherwise joined at least partially along their shaped perimeter.

In accordance with one or more embodiments, front and back panels (1312, 1314) may be formed of natural fibers or synthetic fibers, or a combination thereof. For example, each of front panel 1312 and back panel may be composed of any one of a synthetic polyamide layer such as an aromatic polyamide (e.g., Kevlar®) or an aliphatic polyamide (e.g., nylon), or a natural lignocellulose fiber layer (e.g., bamboo or cotton), or a combination thereof. For example, front panel 1312 may be formed of an aromatic polyamide while back panel 1314 may be formed of bamboo fibers. In addition to the above-identified materials, other suitable natural or synthetic materials known in the art may be utilized, as desired. It should be noted that Kevlar® and nylon represent merely one "species" within the broader "genus" of materials in the respective aromatic polyamide family and aliphatic polyamide family that may be employed for the front and/or back panels (1312, 1314). Similarly, bamboo and cotton represents merely two "species" within the broader "genus" of materials in the lignocellulose fiber family that may be employed for the front and/or back panels (1312, 1314).

The reason for selecting aromatic polyamides (e.g., Kevlar®) for front panel 1312 is as a protective layer. Such aromatic polyamides provide excellent shock absorption and prevent penetration, such as from a sharp or jagged object. A thin protective layer is usually sufficient, as it maintains the requisite strength and flexibility needed by the patient. If the aromatic polyamide layer(s) were made too thick, it may impede the patient from bending forward while wearing the binder apparatus (404) with the support pad.

The reason of selecting aliphatic polyamides (e.g., nylon) for front panel 1312 is as a breathable comfort layer. Such material may be appropriate for a patient who does not expect to need the fall protection described above.

The reason for selecting a natural lignocellulose fiber layer (e.g., bamboo) for back panel 1314 is also as a breathable comfort layer close to the patient's skin. The moisture wicking properties of bamboo fibers make them suitable for longer use in warm weather environments.

Although specific types of materials have been described in connection with front and back panels (1312, 1314), it is to be understood that any other suitable known materials (e.g., polyester, silicone, or others) may be used and are contemplated within the scope of the present disclosure. The choice of material may vary based on desired properties such as durability, flexibility, cushioning, resilience, etc., as needed, and may include other such materials having the one or more of the same or similar properties. Accordingly, the present disclosure is not limited to the materials specifically mentioned, and modifications incorporating alternative materials are intended to be encompassed by this disclosure.

In one or more embodiments, each of the front and back panels (1312, 1314) typically has a thickness in the range of about 0.4 mm (~1/64 inch) to about 3.2 mm (~1/8 inch).

In one or more embodiments, at least two of the intermediate layers (1330) are composed of a polymeric material different from the material of the front and back panels (1312, 1314).

In one or more embodiments, such as depicted in FIGS. 19A-22B, the plurality of intermediate layers (1330) includes two or more layers, which are selected from a group including, but not limited to, a high-density foam layer (e.g., a polyurethane-based high-density foam) 1332, a first elastomer layer (e.g., neoprene) 1334, a second elastomer layer (e.g., vulcanized rubber) 1338, a third elastomer layer (e.g., neoprene) 1340, and a polyethylene layer (e.g., UHMWPE plastic) 1336. The high-density foam layer 1332 has a thickness in the range of about 3.175 mm (~1/8 inch) to about 50.8 mm (~2 inches). The first elastomer layer 1334 has a thickness in the range of about 6.35 mm (~1/4 inch) to about 30 mm (~1.2 inches). The second elastomer layer 1338 has a thickness in the range of about 0.4 mm (~1/64 inch) to about 25.4 mm (~1 inch). The third elastomer layer 1340 has a thickness in the range of about 6.35 mm (~1/4 inch) to about 25.4 mm (~1 inch). The polyethylene layer 1336 has a thickness in the range of about 1.6 mm (~1/16 inch) to about 12.7 mm (~1/2 inch).

In accordance with one or more embodiments, base layer 1350 may be composed of the same material as the above-described high-density foam layer (e.g., a polyurethane-based high-density foam) 1332 or the same material as the above-described first elastomer layer (e.g., neoprene) 1334, or a combination thereof. However, it should be understood that other suitable materials known in the art may also be used, provided they achieve similar properties and functions as described herein. The function of the base layer 1350 is to help disperse internal abdominal pressure by widening the field of the plurality of intermediate layers 1330.

In each of the embodiments, base layer 1350 may be formed as a separate layer from the adjoining core layer or may be initially formed together as a single top-hat shaped layer. The formation of these two adjoining layers can be achieved in a single-step formation through any one or more of different manufacturing processes, including injection molding, 3D printing, and other known methods, or through separate fabrication followed by a fusing step. With separate fabrication, each layer may be formed by any of the aforementioned methods, followed by a thermal welding, adhesive bonding or other known methods for fusing adjoining material layers.

The aforementioned thickness ranges for each material layer are provided as a broader range. More specific sub-ranges may be selected, depending on the desired properties of the patient-specific, custom-made support pad. Although these specific sub-ranges are provided herein, it is understood that alternative ranges may overlap with the specified ranges. Such alternative ranges, even when not explicitly mentioned, are considered within the scope of the embodiments of the present disclosure.

Regarding the front and back panels (1312, 1314), a broader range is described as having a thickness of about 0.4 mm (~1/64 inch) to about 3.2 mm (~1/8 inch). Within the broader range, specific sub-ranges of thickness from which to select include, but are not limited to:

a. about 0.5 mm (~1/48 inch) to about 2.8 mm (~1/9 inch),
b. about 0.6 mm (~1/40 inch) to about 2.5 mm (~1/10 inch), and
c. about 0.7 mm (~1/36 inch) to about 2.1 mm (~1/12 inch).

For patients that require a relatively thinner front and back panels (1312, 1314) (e.g., 0.8 mm (1/32 inch)), additional specific sub-ranges of thickness include, but are not limited to:

a. about 0.4 mm (~1/64 inch) to about 1.2 mm (~1/21 inch),
b. about 0.5 mm (~1/48 inch) to about 1.1 mm (~1/23 inch),
c. about 0.6 mm (~1/40 inch) to about 1.0 mm (~1/25 inch), and
d. about 0.7 mm (~1/36 inch) to about 0.9 mm (~1/28 inch).

For patients that require relatively thicker front and back panels (1312, 1314) (e.g., about 1.6 mm (~1/16 inch)), additional specific sub-ranges of thickness include, but are not limited to:

a. about 1.0 mm (~1/25 inch) to about 3.2 mm (~1/8 inch),
b. about 1.1 mm (~1/23 inch) to about 2.8 mm (~1/9 inch),
c. about 1.2 mm (~1/21 inch) to about 2.5 mm (~1/10 inch),
d. about 1.3 mm (~1/20 inch) to about 2.2 mm (~1/11 inch)
e. about 1.4 mm (~1/18 inch) to about 2.0 mm (~1/13 inch), and
f. about 1.5 mm (~1/17 inch) to about 1.8 mm (~1/14 inch).

Regarding the high-density foam layer 1332, a non-limiting example of which is a high-density polyurethane foam layer, a broader range is described as having a thickness of about 3.175 mm (~1/8 inch) to about 50.8 mm (~2 inches). Within this broader range, general sub-ranges of thickness from which to select include, but are not limited to:

a. about 3.175 mm (~1/8 inch) to about 44 mm (~1.73 inches),
b. about 6.35 mm (~1/4 inch) to about 38 mm (~1.5 inches),
c. about 6.35 mm (~1/4 inch) to about 30 mm (~1.2 inches)
d. about 8.5 mm (~1/3 inch) to about 30 mm (~1.2 inches),
e. about 9.5 mm (~3/8 in.) to about 28 mm (~1.1 inches),
f. about 11 mm (~0.43 inches) to about 25.4 mm (~1 inch),
g. about 12.7 mm (~1/2 inch) to about 22 mm (~7/8 inch), and.
h. about 16 mm (~5/8 inch) to about 20 mm (~0.8 inches).

For patients that require a relatively thinner polyurethane foam layer 1332 (e.g., about 12.7 mm (~1/2 inch)), specific sub-ranges of thickness from which to select include, but are not limited to:

a. about 10 mm (~0.39 inches) to about 16 mm (~5/8 inch), and
b. about 11 mm (~0.43 inches) to about 14 mm (~0.55 inches).

For patients that require a polyurethane foam layer 1332 having a relatively moderate thickness (e.g., about 19 mm (~3/4 inch)), specific sub-ranges of thickness from which to select include, but not limited to:

a. about 14 mm (~0.55 inches) to about 25 mm (~1 inch),
b. about 16 mm (~5/8 inch) to about 22 mm (~7/8 inch), and
c. about 18 mm (~0.71 inches) to about 20 mm (~0.79 inches).

For patients that require a polyurethane foam layer 1332 having a relatively heavy thickness (e.g., about 25.4 mm (~1 inch)), specific sub-ranges of thickness from which to select include, but are not limited to, about 22 mm (~7/8 inch) to about 28 mm (~1.1 inches).

Regarding the first elastomer layer 1334, a non-limiting example of which is a neoprene layer, a broader range is described as having a thickness of about 6.35 mm (~1/4 inch) to about 30 mm (~1.2 inches). Within this broader range, general sub-ranges of thickness from which to select include, but are not limited to:

a. about 7 mm (~0.276 inches) to about 28 mm (~1.1 inches),
b. about 8 mm (~0.315 inches) to about 25 mm (~1 inch),
c. about 9 mm (~0.35 inches) to about 22 mm (~7/8 inch),
d. about 10 mm (~0.39 inches) to about 19 mm (~3/4 inch),
e. about 11 mm (~0.43 inches) to about 16 mm (~5/8 inch), and
f. about 12 mm (~0.47 inches) to about 14 mm (~0.55 inches).

For patients that require a relatively thinner first elastomer layer 1334 (e.g., about 9.5 mm (~3/8 inch)), specific sub-ranges of thickness from which to select include, but are not limited to:

a. about 6.35 mm (~1/4 inch) to about 12.7 mm (~1/2 inch), and b. about 8 mm (~0.315 inches) to about 11 mm (~0.43 inches).

For patients that require a relatively slightly thicker first elastomer layer 1334 (e.g., about 12.7 mm (½ inch)), specific sub-ranges of thickness from which to select include, but are not limited to:

a. about 10 mm (~0.39 inches) to about 16 mm (~⅝ inch), and b. about 11 mm (~0.43 inches) to about 14 mm (~0.55 inches).

For patients that require a first elastomer layer 1334 having a moderate thickness (e.g., about 19 mm (¾ in.)), specific sub-ranges of thickness from which to select include, but are not limited to:

a. about 14 mm (~0.55 inches) to about 25 mm (~1 inch), b. about 16 mm (~⅝ inch) to about 22 mm (~⅞ inch), and c. about 18 mm (~0.71 inches) to about 20 mm (~0.79 inches).

For patients that require a first elastomer layer 1334 having a heavier thickness (e.g., about 25 mm (~1 inch) or about 29 mm (~1.125 inches)), specific sub-ranges of thickness from which to select include, but are not limited to, about 22 mm (~0.87 inches) to about 30 mm (~1.2 inches).

Regarding the second elastomer layer 1338, a non-limiting example of which is a vulcanized rubber layer, a broader range is described as having a thickness of about 0.4 mm (~1/64 inch) to about 25.4 mm (~1 inch). Within the broader range, specific sub-ranges of thickness from which to select include, but are not limited to:

a. about 3.175 mm (~⅛ inch) to about 22 mm (~⅞ inch), b. about 6.35 mm (~¼ inch) to about 19 mm (~¾ inch), c. about 9 mm (~0.35 inches) to about 18 mm (~0.7 inches), d. about 10 mm (~0.39 inches) to about 16 mm (~⅝ inch), and e. about 11 mm (~0.43 inches) to about 14 mm (~0.55 inches).

For patients that require a relatively thinner second elastomer layer 1338 (e.g., about 9.5 mm (~⅜ in.)), specific sub-ranges of thickness from which to select include, but are not limited to:

a. about 6 mm (~0.24 inch) to about 13 mm (~0.51 inch), b. about 7 mm (~0.276 inches) to about 12 mm (~0.48 inches), and c. about 8 mm (~0.315 inches) to about 11 mm (~0.43 inches).

For patients that require a second elastomer layer 1338 having a relatively moderate thickness (e.g., about 12.7 mm (~½ inch)), specific sub-ranges of thickness from which to select include, but are not limited to:

a. about 10 mm (~0.39 inches) to about 16 mm (~⅝ inch), and b. about 11 mm (~0.43 inches) to about 14 mm (~0.55 inches).

For patients that require a second elastomer layer 1338 having a having a heavier thickness (e.g., about 16 mm (~⅝ inch)), specific sub-ranges of thickness from which to select include, but are not limited to:

a. about 9.5 mm (~⅜ inch) to about 22 mm (~⅞ inch), b. about 12.7 mm (~½ inch) to about 19 mm (¾ inch), and c. about 14 mm (~0.55 inches) to about 18 mm (~0.7 inches).

Regarding the third elastomer layer 1340, a non-limiting example of which is a second neoprene layer, a broader range is described as having a thickness of about 6.35 mm (~¼ inch) to about 19 mm (~¾ inch). Within this broader range, general sub-ranges of thickness from which to select include, but are not limited to:

a. about 9.5 mm (~⅜ inch) to about 16 mm (~⅝ inch), and b. about 11 mm (~0.43 inches) to about 14 mm (~0.55 inches).

Regarding the polyethylene layer 1336, a non-limiting example of which is a UHMWPE layer, a broader range is described as having a thickness of about 1.6 mm (~1/16 inch) to about 12.7 mm (~½ inch). Within this broader range, general sub-ranges of thickness from which to select include, but are not limited to:

a. about 2 mm (~1/13 inch) to about 12 mm (~0.47 inches), b. about 2.54 mm (1/10 inch) to about 11 mm (~0.43 inches), c. about 2.88 mm (~1/9 inch) to about 10 mm (~0.39 inches), d. about 3.175 mm (~⅛ inch) to about 9.5 mm (~⅜ inch), e. about 4.2 mm (~⅙ inch) to about 8.5 mm (~⅓ inch), and f. about 5 mm (~⅕ inch) to about 7.6 mm (0.3 inches).

For patients that require a relatively thinner polyethylene layer 1336 (e.g., 3.175 mm (~⅛ inch)), specific sub-ranges of thickness from which to select include, but are not limited to:

a. about 1.6 mm (~1/16 inch) to about 6.35 mm (~¼ inch), b. about 2 mm (~1/13 inch) to about 5 mm (~⅕ inch), c. about 2.54 mm (1/10 inch) to about 4.2 mm (~⅙), and d. about 2.88 mm (~1/9 inch) to about 3.6 mm (~0.14 inches).

For patients that require a polyethylene layer 1336 having a relatively moderate thickness (e.g., 6.35 mm (~¼ inch)), specific sub-ranges of thickness from which to select include, but are not limited to:

a. about 3.175 mm (~⅛ inch) to about 9.5 mm (~⅜ inch), b. about 4.2 mm (~⅙ inch) to about 8.5 mm (~⅓ inch), and c. about 5 mm (~⅕ inch) to about 7.6 mm (0.3 inches).

For patients that require a polyethylene layer 1336 having a relatively heavy thickness (e.g., about 9.5 mm (~⅜ inch)), specific sub-ranges of thickness from which to select include, but are not limited to:

a. about 6.35 mm (~¼ inch) to about 12.7 mm (~½ inch);

b. about 7.6 mm (0.3 inches) to about 11 mm (~0.43 inches), and c. about 8.5 mm (~⅓ inch) to about 10 mm (~0.39 inches), Regarding the base layer 1350, a broader range is described as having a thickness of about 6.35 mm (~¼ inch) to about 38 mm (~1.5 inches). Within this broader range, general sub-ranges of thickness from which to select include, but are not limited to:

a. about 9.5 mm (~⅜ inch) to about 25.4 mm (~1 inch); and b. about 12.7 mm (~½ inch) to about 19 mm (¾ inch.

The aforementioned ranges are selected according to the specific needs of each patient. These needs vary according to the body type of the patient, the nature of the hernia (e.g., size, location, severity). The selection of materials and their thickness ranges also depends on the anticipated level of the patient's day-to-day activities.

The horizontal dimensions (length and width) of support pad 1300 depend on the size of incision, the size of the mesh, the body type of the patient and the physical activities expected of the patient. Such physical activities are a factor in dictating the level and type of support needed by the patient from support pad 1300. In accordance with some of the above-described embodiments, the intermediate layers 1330 are sized according to the size of the incision. A base layer 1350 is provided having a margin portion 1352 that extends laterally beyond the horizontal dimensions (length and width) of the surgical incision, such as between one to two inches.

Body types or somatotypes are hereditary traits based on one's skeletal frame (bone structure and density) and body composition (muscle and fat mass). The different body types include ectomorph, mesomorph and endomorph. Ectomorphs typically have a lean and slender build with narrow shoulders and hips and a flat chest. They tend to have a fast metabolism, making it challenging for them to gain weight or muscle mass. Mesomorphs have a more muscular and athletic physique, with a naturally higher percentage of muscle mass. They often have a broader shoulder-to-hip ratio, making it relatively easier for them to gain and maintain muscle. Endomorphs generally have a softer and rounder body—i.e., they are typically short and stocky with large shoulder—with a higher tendency to store body fat. They may find it easier to gain weight, both in terms of muscle and fat. The aforementioned categories are broad, and many people exhibit a combination of these body types rather than fitting strictly into one category.

Ectomorphs generally require less rebound resilience due to their leaner frame. By contrast, mesomorphs and endomorphs typically require more rebound resilience due to their bulkier frames. Additionally, mesomorphs and endomorphs who possessed a well-developed musculature pre-injury are likely to undergo intensive physiotherapy post-surgery to regain their prior physique. Such intensive exercise may be difficult for the patient, thus requiring support pads having excellent rebound resilience. On the other hand, mesomorphs and endomorphs that have an average-to-overweight physique may require rebound resilience to assist them in everyday tasks, but less than compared to their more muscular counterparts.

As will be described below, rebound resilience is provided in the support pads by a polyethylene layer 1336 (e.g., a UHMWPE layer) or a second elastomer layer 1338 (e.g., vulcanized rubber), or a combination thereof. The selection of other intermediate layers, such as a high-density foam layer 1332 (e.g., a polyurethane high-density foam layer) for shock absorption and first and third elastomer layers (1334, 1340) (e.g., neoprene layers) for cushioning support is determined on a case-by-case basis to optimize patient comfort (as described below). Additionally, embodiments are described above in connection with FIG. 10, which illustrates the positioning of air bag/bladder 1004 in such manner that it will provide lumbar support. In particular, bladder 1004 provides a counterforce to the patient's spine, which assists the patient with rebound. Thus, bladder 1004 may supplement the rebound resilience provided by either, or both of, polyethylene layer 1336 and second elastomer layer 1338.

In the multilayered support pads (1900-2210) depicted in respective FIGS. 19A-22B, some of the layers are identified by specific material or species. These materials are intended to be representative examples within a broader class of suitable materials. It should be understood that the reference to a particular material in the drawings is not intended to limit the present disclosure to that specific material, but rather to illustrate one possible embodiment within a larger family or genus of materials. Each named layer may optionally be formed with one or more additional materials. These additional materials may be selected to provide properties beneficial for the intended application, allowing for tailored performance characteristics without departing from the primary functional qualities of the named material layer.

Regarding the intermediate layers (1330), the figures identify the polyurethane foam layer 1332 as being composed of high-density foam, the first and third elastomer layers (1334, 1340) as being composed of neoprene (polychloroprene), the second elastomer layer as being composed of vulcanized rubber, and the polyethylene layer as being composed of UHMW (ultra high molecular weight) plastic, also referred to as UHMWPE. In each of these examples, the figures merely represent one "species" within the broader genus of materials that may be employed for that layer.

The first elastomer layer 1334 may also be referred to as a compressible elastomer layer. The second elastomer layer 1338 may also be referred to as a resilient elastomer layer. The third elastomer layer 1340 may also be referred to as another compressible elastomer layer.

The present disclosure contemplates the use of any material within the described broader genus that possesses the necessary properties and characteristics required for the layer in question. Accordingly, the description and the accompanying drawings are to be interpreted as illustrative rather than restrictive, and it is intended that all suitable materials within the identified genera are within the scope of the present disclosure. Other materials known in the art that exhibit similar properties and characteristics are also contemplated within the scope of the present disclosure.

In each of the support pads (1900-2120) depicted in respective FIGS. 19A-21C, a high-density foam layer 1332 is provided adjacent to front panel 1312 (the outside facing side). (In other embodiments, the high-density foam layer 1332 is provided proximate to front panel 1312, with one or more intervening layers of other materials.) In one or more embodiments, the high-density foam layer 1332 is comprised of a material selected from a genus of suitable materials. As a non-limiting example, the material is composed of high-density polyurethane foam, although other suitable materials within the same genus may also be used without departing from the scope of the present disclosure. The selection of the material for high-density foam layer 1332 may be based on relevant properties such as, but not limited to, high tensile strength and shock absorbency, to achieve the desired performance characteristics. For instance, the arrangement of a polyurethane foam layer 1332 close to the outside facing side of the support pad (i.e., close to the front panel 1312) provides an initial shock absorbent layer to prevent an external force from traveling to the hernia site.

In each of the support pads (1900-2210) depicted in respective FIGS. 19A-22B, a first elastomer layer 1334 is provided adjacent to back panel 1314 (the patient-facing side). (In other embodiments, the first elastomer layer is provided proximate to back panel 1314, with one or more intervening layers of other materials.) In one or more embodiments, first elastomer layer 1334 is comprised of a material selected from a genus of suitable materials. As a non-limiting example, the material is composed of neoprene, although other suitable materials within the same genus may also be used (e.g., another foam rubber) without departing from the scope of the present disclosure. The selection of the material for the first elastomer layer 1334 may be based on relevant properties such as, but not limited to, high elasticity. For instance, the arrangement of the first elastomer layer 1334 proximate to the hernia site (i.e., the closest of the intermediate layers 1330 to the hernia site) provides an easily deforming cushioning layer. First elastomer layer 1334 is typically a relatively thick, softer foam layer, whereas a more rigid foam layer may apply undue pressure to the hernia site.

As described above, FIG. 16 illustrates an embodiment having a core layer 1332 (e.g., a polyurethane foam layer) proximate to the outside-facing side of support pad 1300 and a core layer 1334 (e.g., a first elastomer layer) proximate to the patient-facing side of support pad 1300. The high-density foam layer (1332), which resists compression, helps distribute any applied pressure or impact over a wider area before it reaches the softer, low-density layer (1334). This configuration is beneficial when a firm, supportive surface is desired, with a slight cushioning effect beneath it.

In alternate embodiments, such as where the cushioning effect is not required (e.g., the patient having a bulkier midsection), the low-density first elastomer layer (1334) may be replaced with a high-density layer (1332). In such an embodiment, the support pad may include two high-density foam layers-one proximate or adjacent to the front panel (1312) and the other proximate or adjacent to the back panel (1314), with two or more additional intermediate layers there between. The additional layers include a polyethylene layer (1336), a second elastomer layer (1338), or both. A first elastomer layer (1334) may be provided between the two high-density layers (1332).

In each of the support pads (1910, 2000, 2100, 2120, 2200, 2210) depicted in respective FIGS. 19B, 20, 21A, 21C and 22A-22B, the second elastomer layer 1338 is provided adjacent first elastomer layer 1334. (In other embodiments, the second elastomer layer (1338) is provided proximate to the first elastomer layer (1334), with one or more intervening layers of other materials.) In one or more embodiments, second elastomer layer 1338 is comprised of a material selected from a genus of suitable materials. As a non-limiting example, the material is composed of vulcanized rubber, although other suitable materials within the same genus may also be used without departing from the scope of the present disclosure. The selection of the material for the second elastomer layer 1338 may be based on relevant properties such as, but not limited to, rebound resilience and shock absorbency, to achieve desired performance characteristics.

Vulcanization is defined, in the context of the present disclosure, as a process that increases the retractile force and reduces the amount of permanent deformation remaining after removal of the deforming force. Thus, vulcanization increases elasticity while it decreases plasticity. This is generally accomplished by the formation of a cross-linked molecular network. Using vulcanized rubber as a non-limiting example, the second elastomer layer 1338 has a cross-linked structure that has controlled elasticity, meaning it can stretch and return to its original shape without excessive rebound, providing a more consistent and stable response. Furthermore, the cross-linked structure allows it to absorb and dissipate energy more efficiently. This energy absorption capability helps in reducing the amount of energy that is returned during the rebound phase, thus minimizing the rebound effect.

In practice, second elastomer layer 1338 may assist a patient in returning to an upright position (~180 degrees) from a bent-over position (e.g., ~90 degrees). More specifically, second elastomer layer 1338 has sufficient elasticity to allow the user to initially transition to the bent-over orientation (e.g., to ~90 degrees), but with enough elastic recovery to add its own force of recovery to the patient as they attempt to straighten up (to ~180 degrees).

The choice of including the second elastomer layer 1338 depends on multiple factors, including, but not limited to, the body type musculature of the patient. For example, a patient that is slim and very fit has a lighter torso and doesn't require as much resistance to avoid rebound. More specifically, such patient may not require the elastic recovery assistance.

The second elastomer layer 1338 generally has a higher stiffness and lower flexibility as compared with the first elastomer layer 1334. Due to these properties, the second elastomer layer 1338 typically has a reduced thickness as compared with the first elastomer layer 1334 to avoid producing a stiffened composite support pad.

Substitute materials for the second elastomer layer 1338, which should feature the aforementioned properties, may include, but are not limited to, silicone rubber, polyurethane foam, latex rubber, and SBR rubber (Styrene-Butadiene rubber). A person having ordinary skill in the art would consider the differences between vulcanized rubber and the aforementioned substitute materials when selecting an appropriate thickness of the substitute material for second elastomer layer 1338.

Figure 21A:
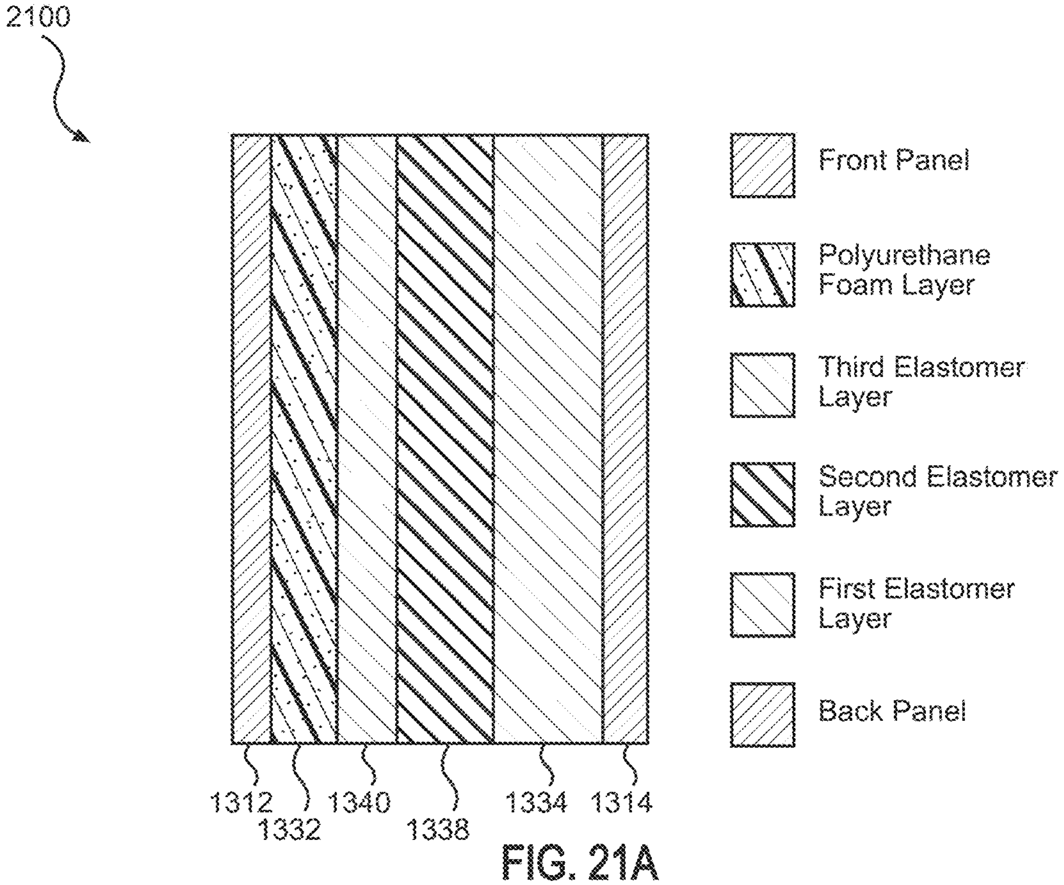
FIGS. 21A-21C illustrate cross-section views of multilayered support pad inserts in accordance with one or more embodiments of the present disclosure.
Figure 21B:
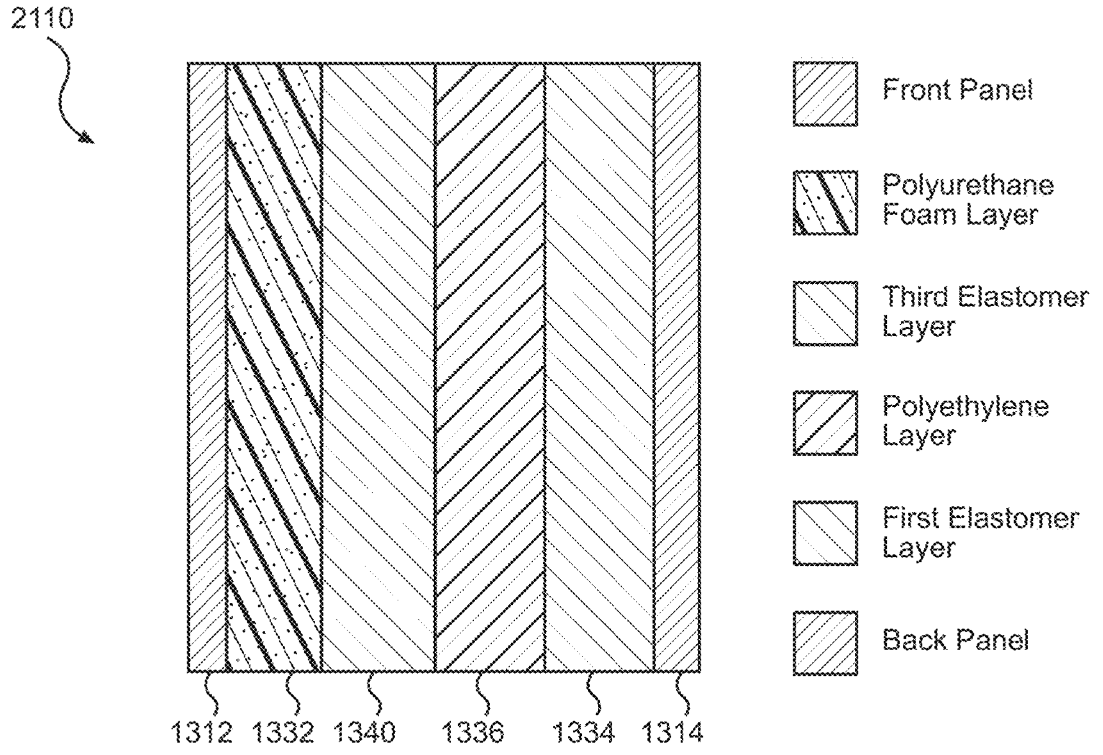
Figure 21C:
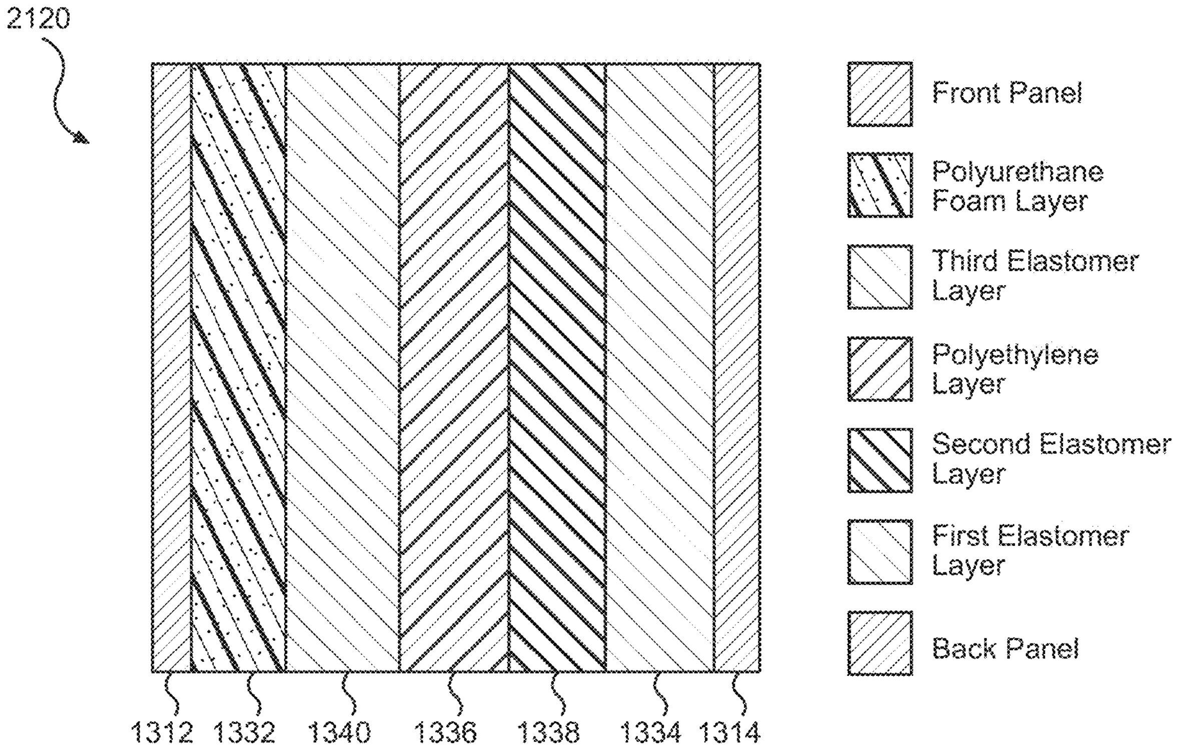

In each of the support pads (2100, 2110 and 2120) depicted in respective FIGS. 21A-21C, a third elastomer layer 1340 is provided adjacent the polyurethane foam layer 1332. (In other embodiments, the third elastomer layer (1340) is provided proximate to the polyurethane foam layer (1332), with one or more intervening layers of other materials.) In one or more embodiments, third elastomer layer 1340 is comprised of a material selected from a genus of suitable materials. As a non-limiting example, the material is composed of neoprene, although other suitable materials within the same genus may also be used (e.g., another foam rubber) without departing from the scope of the present disclosure. The selection of the material for third elastomer layer 1340 may be based on relevant properties such as, but not limited to, high elasticity, to achieve the desired performance characteristics. For instance, the arrangement of third elastomer layer 1340 proximate or adjacent to the polyurethane foam layer 1332 provides additional cushioning towards the outside-facing side of the support pad; that is, third elastomer layer 1340 may reinforce the shock absorbency of polyurethane foam layer 1332.

In each of the support pads (1900, 2000, 2110, 2120, 2200) depicted in respective FIGS. 19A, 20, 21B-21C and 22A, a polyethylene layer 1336 is provided adjacent to first elastomer layer 1334 and/or the second elastomer layer 1338. In particular, polyethylene layer 1336 may be provided (i) adjacent to the first elastomer layer 1334 (see FIGS. 19A and 21B), (ii) adjacent to the second elastomer layer 1338—when the latter is adjacent to first elastomer layer 1334 (see FIGS. 20, 21C and 22A), (iii) in between the first and third elastomer layers (1334, 1340) (see FIGS. 21B and 21C), or (iv) between the first and second elastomer layers (1334, 1338) (not shown). (In other embodiments, polyethylene layer 1336 is provided proximate to the aforementioned alternative layers, with one or more intervening layers of other materials.) In one or more embodiments, polyethylene layer 1336 is comprised of a material selected from a genus of suitable materials. As a non-limiting example, the material is composed of UHMW plastic, although other suitable materials within the same genus may also be used without departing from the scope of the present disclosure. The selection of the material for polyethylene layer 1336 may be based on relevant properties such as, but not limited to, rebound resilience, to achieve the desired performance characteristics. In particular, the polyethylene layer 1336 provides excellent rebound resilience for posture and prevents distension of the hernia. When polyethylene layer 1336 is composed of UHMW, it is typically configured with a thinner profile compared to other individual layers of the intermediate layers (1330), as the increased thickness of UHMW plastic may hinder the ability of the support pad to flex properly (i.e., it may resist compression). If another type of polyethylene plastic were selected, its thickness may vary somewhat from the thickness ranges described herein, depending on the elasticity and rebound resilience of the selected substitute material. A person having ordinary skill in the art would consider such differences when selecting the appropriate thickness of the substitute material for polyethylene layer 1336.

In embodiments in which a polyethylene layer (1336) and a second elastomer layer (1338) is provided, the support pad maintains sufficient rigidity to keep the hernia mesh from distending and also helps with rebound and resuming correct vertical posture.

Similar to the second elastomer layer 1338 (described above), the polyethylene layer 1336 has excellent rebound resilience, thereby assisting a patient in returning to an upright position (~180 degrees) from a bent-over position (e.g., ~90 degrees). A person having ordinary skill in the art would understand that the combined use of the second elastomer layer 1338 and the polyethylene layer 1336 may result in too much rebound resilience, whereby a patient without sufficient musculature may have difficulty overcoming such resistance to bend over initially. Accordingly, in some instances, depending on the patient's need, it may be necessary to omit either the polyethylene layer 1336 layer or the second elastomer layer 1338, or to reduce the thickness of each layer if both are included in the support pad.

In the embodiments depicted in the figures, specific layers are shown as being directly adjacent to one another. However, it is understood that in alternate embodiments, additional layers may be interposed between these identified layers. Accordingly, the term "adjacent" or "proximate" as used herein refers to the spatial relationship between the layers as originally identified, even if one or more additional layers are interposed between them.

Figure 19A:
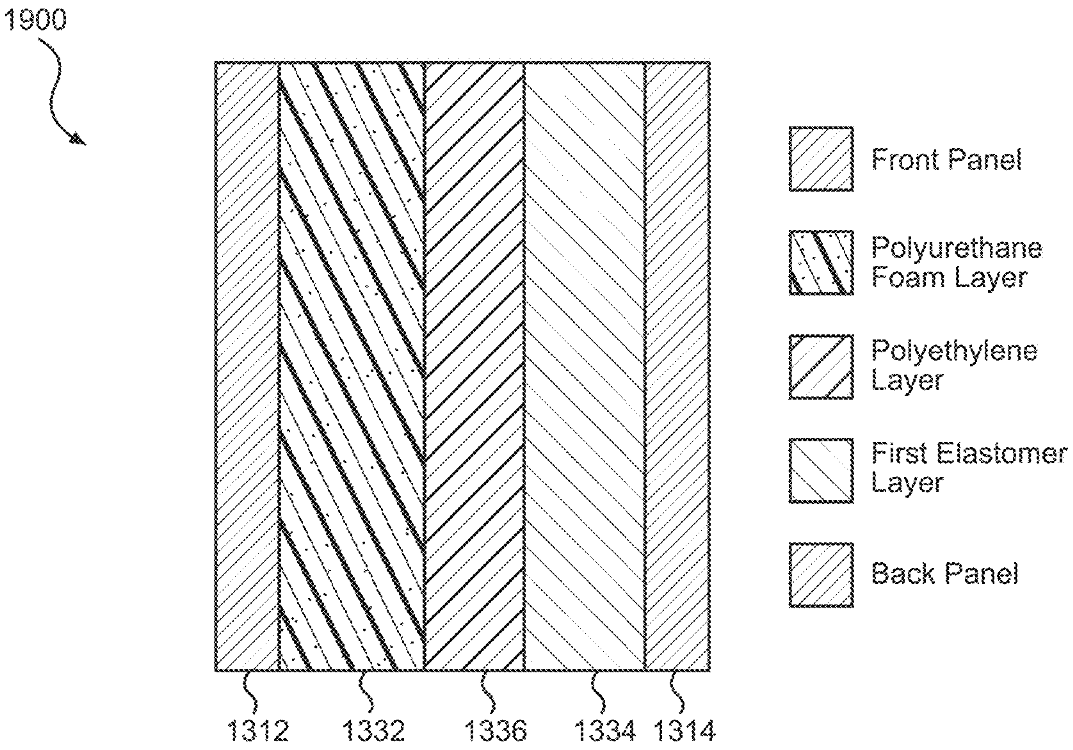
FIGS. 19A-19B illustrate cross-section views of multilayered support pad inserts in accordance with one or more embodiments of the present disclosure.
Figure 19B:
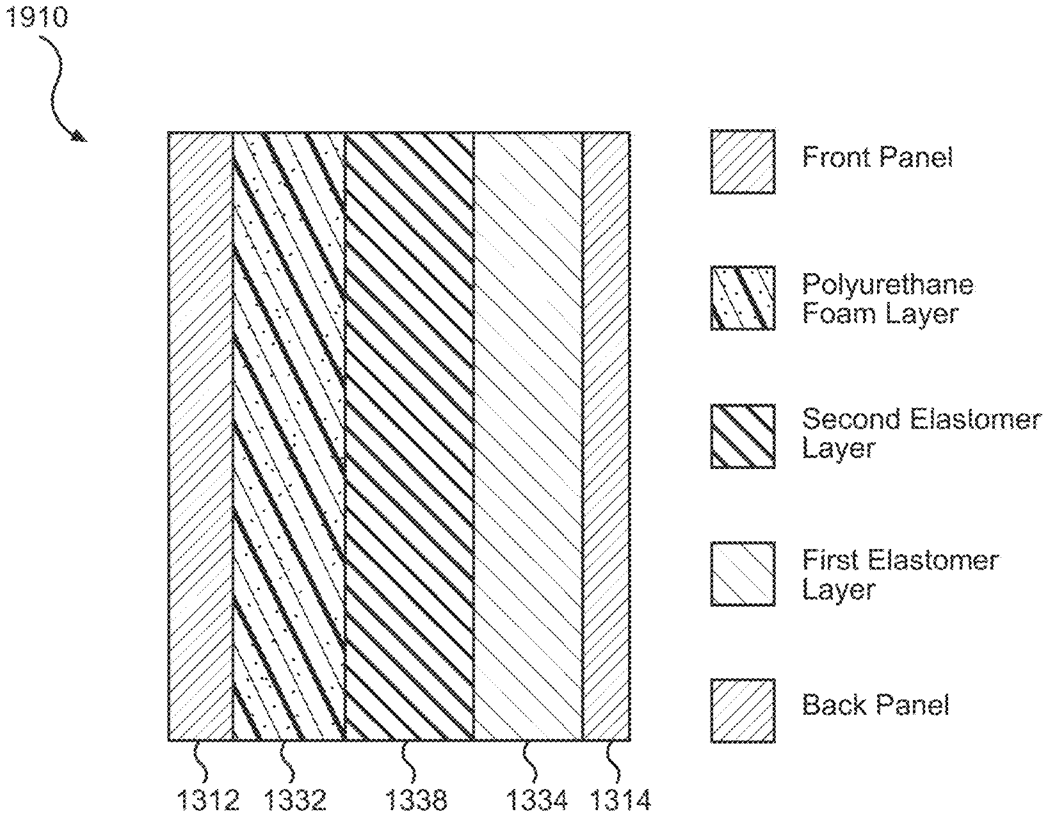

For example, in alternate embodiments of the support pads (1900, 1910) depicted in respective FIG. 19A-19B, an additional layer may be introduced between front panel (1312) and polyurethane foam layer (1332). Despite the presence of this interposed layer, front panel (1312) and polyurethane foam layer (1332) may still be considered proximate or adjacent within the context of this description. The terms "adjacent" and "proximate" are therefore to be interpreted as indicating that the layers are positioned in relative close proximity to one another, either directly or with the potential for one or more interposing layers.

In each of the support pads (1900-2120) depicted in respective FIGS. 19A-21C, the intermediate layers are shown to include a polyurethane foam layer 1332 and a first elastomer layer 1334. In these embodiments, the polyurethane foam layer 1332 is proximate or adjacent to front panel 1312 and the first elastomer layer 1334 is proximate or adjacent to back panel 1314. Furthermore, in each the support pads (1900-2120) depicted in respective FIGS. 19A-21C, one or both of a polyethylene layer 1336 and a second elastomer layer 1338 are positioned between the polyurethane foam layer 1332 and the first elastomer layer 1334. Further details of these figures are provided below.

FIG. 19A illustrates, in accordance with one or more embodiments, a multilayered support pad 1900 having a front panel 1312, a polyurethane foam layer 1332 adjacent to front panel 1312, a polyethylene layer 1336 adjacent to polyurethane foam layer 1332, a first elastomer layer 1334 adjacent to polyethylene layer 1336, and a back panel 1314 adjacent to first elastomer layer 1334.

Support pad 1900, as described above and further detailed in Tables 2-3 below, is exemplarily suited for patients having a muscular ectomorph physique. Such a patient is slim, very fit and has a lighter torso and thus does not require much resistance to minimize the rebound effect, as compared with the support pads of some of the other embodiments. Accordingly, this patient may not require a second elastomer layer (1338) in addition to the present polyethylene layer (1336).

FIG. 19B illustrates, in accordance with one or more embodiments, a multilayered support pad 1910 similar to support pad 1900 described above in connection with FIG. 19A, with the primary difference being the substitution of polyethylene layer 1336 (in support pad 1900 in FIG. 19A) with second elastomer layer 1338 (in support pad 1910 in FIG. 19B). In FIG. 19B, the other elements of the intermediate layers—i.e., polyurethane foam layer 1332 and first elastomer layer 1334—correspond to those previously described in FIG. 19A, serving the same function and structure. Second elastomer layer 1338, however, replaces polyethylene layer 1336. Accordingly, second elastomer layer 1338 is shown adjacent to polyurethane foam layer 1332 on its left and adjacent to first elastomer layer 1334 on its right.

Support pad 1910, as described above and further detailed in Tables 2-3 below, is exemplarily suited for patients having a muscular ectomorph physique. Such a patient is slim, very fit and has a lighter torso and thus does not require much resistance to avoid rebound, as compared with the support pads of some of the other embodiments. Accordingly, this patient may not require a polyethylene layer (1336) in addition to the present second elastomer layer 1338. It should be noted that second elastomer layer 1338 may be thicker (in the embodiment shown in FIG. 19B) than the corresponding polyethylene layer 1336 (in the embodiment shown in FIG. 19A) due to the known higher rebound resilience of polyethylene layer (1336) as compared with second elastomer layer 1338. In an alternate embodiment of support pad 1910, both of the second elastomer layer (1338) and the polyethylene layer (1336) is provided, each having a reduced thickness to avoid unnecessary stiffness.

Figure 20:
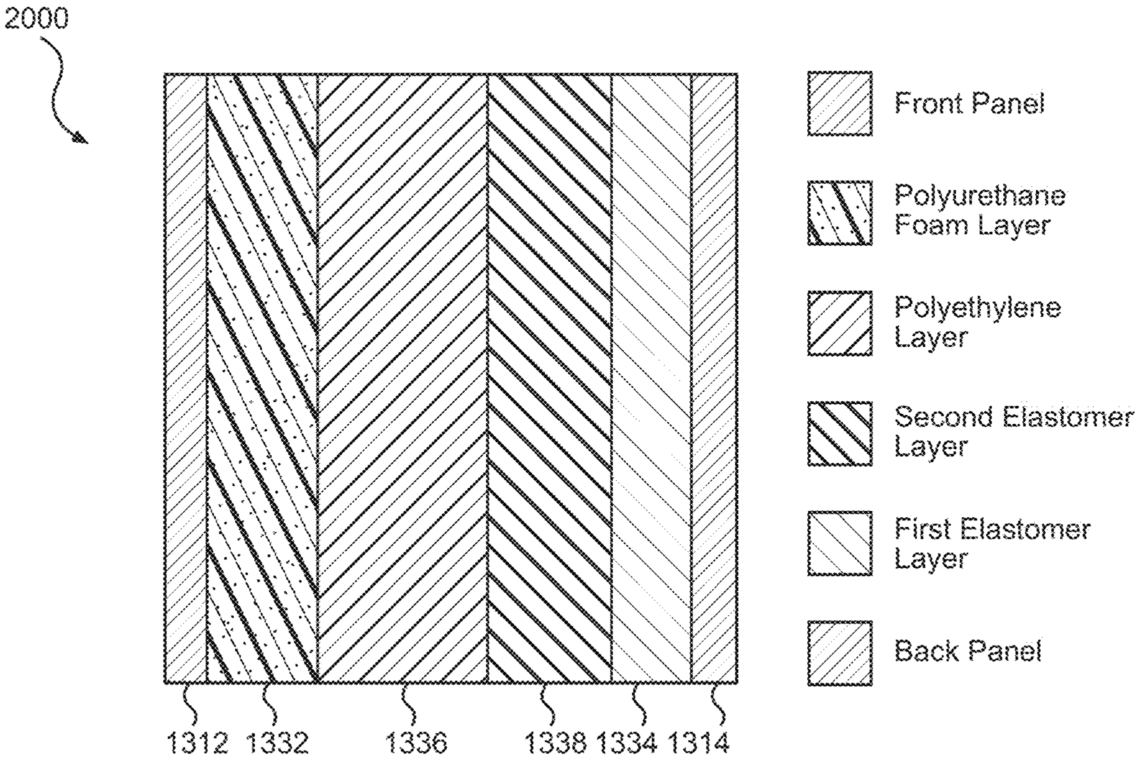
FIG. 20 illustrates a cross-section views of a multilayered support pad insert in accordance with one or more embodiments of the present disclosure.

FIG. 20 illustrates, in accordance with one or more embodiments, a multilayered support pad 2000 similar to the support pads (1900, 1910) described above in connection with FIGS. 19A-19B, with the primary difference being the inclusion of both polyethylene layer 1336 (see FIG. 19A) and second elastomer layer 1338 (see FIG. 19B). Accordingly, support pad 2000 has a front panel 1312, a polyurethane foam layer 1332 adjacent to front panel 1312, a polyethylene layer 1336 adjacent to polyurethane foam layer 1332, a second elastomer layer 1338 adjacent to polyethylene layer 1336, a first elastomer layer 1334 adjacent to second elastomer layer 1338, and a back panel 1314 adjacent to first elastomer layer 1334.

FIG. 20 depicts a first arrangement, wherein polyethylene layer 1336 is positioned relatively closer to the outside-facing side and second elastomer layer 1338 is positioned relatively closer to the patient-facing side, as described above. In this configuration, support pad 2000 is more flexible and less resilient. However, it is to be understood that a second arrangement is also contemplated within the scope of the present disclosure, in which the positions of polyethylene layer (1336) and second elastomer layer (1338) are switched, such that the second elastomer layer (1338) is positioned relatively closer to the outside-facing side and the polyethylene layer (1336) is positioned relatively closer to the patient-facing side. In this configuration, support pad (2000) is more resilient and less flexible.

Support pad 2000, as described above and further detailed in Tables 2-3 below, is exemplarily suited for patients of varying physiques, depending on the thickness of each material layer as described in each embodiment. With reference to Tables 2-3 below, variations of support pad 2000 may be suitable for a muscular mesomorph (Emb. [4]), a portly endomorph (Emb. [5]), an average-stocky mesomorph (Emb. [6]), a thin-muscular ectomorph (Emb. [7]), and an average mesomorph (Emb. [8]).

FIGS. 21A-21C illustrate a plurality of embodiments in which the third elastomer layer 1517 is added to the respective multilayered support pad (2100, 2110, 2120).

FIG. 21A illustrates, in accordance with one or more embodiments, a multilayered support pad 2100 similar to support pad 1910 described above in connection with FIG. 19B, with the primary difference being the inclusion of a third elastomer layer 1340 positioned between a polyurethane foam layer 1332 and a second elastomer layer 1338. Accordingly, support pad 2100 has a front panel 1312, a polyurethane foam layer 1332 adjacent to front panel 1312, a third elastomer layer 1340 adjacent to polyurethane foam layer 1332, a second elastomer layer 1338 adjacent to third elastomer layer 1340, a first elastomer layer 1334 adjacent to second elastomer layer 1338, and a back panel 1314 adjacent to first elastomer layer 1334.

FIG. 21B illustrates, in accordance with one or more embodiments, a multilayered support pad 2110 similar to support pad 1900 described above in connection with FIG. 19A, with the primary difference being the inclusion of a third elastomer layer 1340 positioned between a polyurethane foam layer 1332 and a polyethylene layer 1336. Accordingly, support pad 2110 has a front panel 1312, a polyurethane foam layer 1332 adjacent to front panel 1312, a third elastomer layer 1340 adjacent to polyurethane foam layer 1332, a polyethylene layer 1336 adjacent to third elastomer layer 1340, a first elastomer layer 1334 adjacent to polyethylene layer 1336, and a back panel 1314 adjacent to first elastomer layer 1334.

FIG. 21C illustrates, in accordance with one or more embodiments, a multilayered support pad 2120 similar to support pads (1900, 1910) described above in connection with FIGS. 19A-19B, with the primary difference being the inclusion of both polyethylene layer 1336 (see FIG. 19B) and second elastomer layer 1338 (see FIG. 19A). Accordingly, support pad 2120 has a front panel 1312, a polyurethane foam layer 1332 adjacent to front panel 1312, a third elastomer layer 1340 adjacent to polyurethane foam layer 1332, a polyethylene layer 1336 adjacent to third elastomer layer 1340, a second elastomer layer 1338 adjacent to polyethylene layer 1336, a first elastomer layer 1334 adjacent to second elastomer layer 1338, and a back panel 1314 adjacent to first elastomer layer 1334.

FIG. 21C depicts a first arrangement, wherein polyethylene layer 1336 is positioned relatively closer to the outside-facing side and second elastomer layer 1338 is positioned relatively closer to the patient-facing side, as described above. In this configuration, support pad 2120 is more flexible and less resilient. However, it is to be understood that a second arrangement is also contemplated within the scope of the present disclosure, in which the positions of polyethylene layer (1336) and second elastomer layer (1338) are switched, such that the second elastomer layer (1338) is positioned relatively closer to the outside-facing side and the polyethylene layer (1336) is positioned relatively closer to the patient-facing side. In this configuration, support pad (2120) is more resilient and less flexible.

Figure 22A:
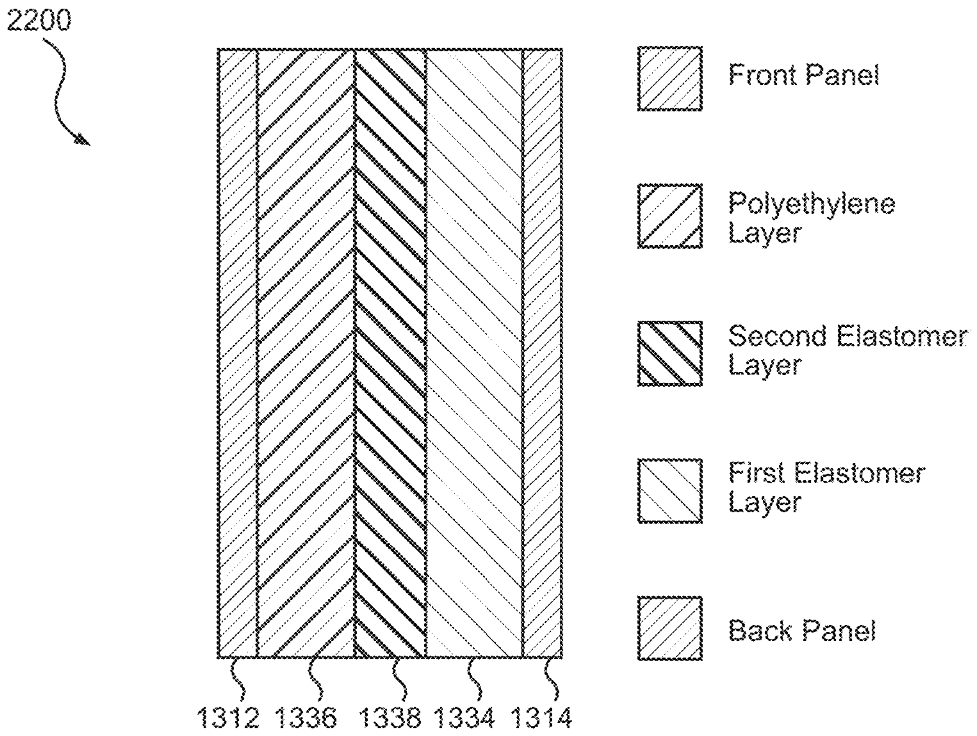
FIGS. 22A-22B illustrate cross-section views of multilayered support pad inserts in accordance with one or more embodiments of the present disclosure.

FIG. 22A illustrates, in accordance with one or more embodiments, a multilayered support pad 2200 similar to support pad 2000 described above in connection with FIG. 20, with the primary difference being the absence of the polyurethane foam layer (1332). Accordingly, support pad 2200 has a front panel 1312, a polyethylene layer 1336 adjacent to front panel 1312, a second elastomer layer 1338 adjacent to polyethylene layer 1336, a first elastomer layer 1334 adjacent to second elastomer layer 1338, and a back panel 1314 adjacent to first elastomer layer 1334.

FIG. 22A depicts a first arrangement, wherein polyethylene layer 1336 is positioned relatively closer to the outside-facing side and second elastomer layer 1338 is positioned relatively closer to the patient-facing side, as described above. In this configuration, support pad 2200 is more flexible and less resilient. However, it is to be understood that a second arrangement is also contemplated within the scope of the present disclosure, in which the positions of polyethylene layer (1336) and second elastomer layer (1338) are switched, such that the second elastomer layer (1338) is positioned relatively closer to the outside-facing side and the polyethylene layer (1336) is positioned relatively closer to the patient-facing side. In this configuration, support pad (2200) is more resilient and less flexible.

Figure 22B:
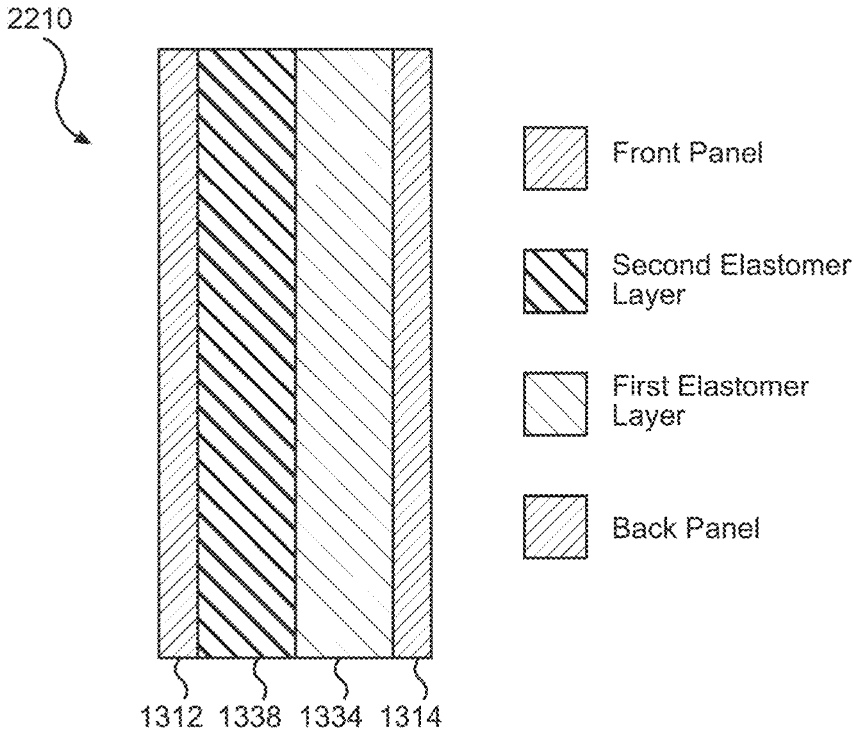

FIG. 22B illustrates, in accordance with one or more embodiments, a multilayered support pad 2210 similar to support mad 2200 described above in connection with FIG. 22A, with the primary difference being the absence of the polyethylene layer (1336). Accordingly, support pad 2210 has a front panel 1312, a second elastomer layer 1338 adjacent to front panel 1312, a first elastomer layer 1334 adjacent to second elastomer layer 1338, and a back panel 1314 adjacent to first elastomer layer 1334.

The various embodiments of the multilayered support pads described above are summarized in the following Tables 1-2. The presence of a material layer is indicated with an "X" or at least one alphanumeric value, while the absence of a layer is indicated with "--."

TABLE 1 provides a comparison of the composition of the intermediate layers (1330) of the supports pads (1900-2210) depicted in FIGS. 19A-22B.

TABLE 1

Composition of the intermediate layers in FIGS. 19A-22B

| FIG. | 1st Elast. layer | 2nd Elast. layer | 3rd Elast. layer | PU foam layer | PE layer |
|---|---|---|---|---|---|
| 19A | X | — | — | X | X |
| 19B | X | X | — | X | — |
| 20 | X | X | — | X | X |
| 21A | X | X | X | X | — |
| 21B | X | — | X | X | X |
| 21C | X | X | X | X | X |
| 22A | X | X | — | — | X |
| 2B | X | X | — | — | — |

TABLE 2 provides a comparison of exemplary, approximate thickness values for each of layer in the multilayered support pads depicted in FIGS. 19A-22B.

TABLE 2

| Exemplary (approx.) thickness of each of layer in FIGS. 13A-16B | | | | | | | | |
|---|---|---|---|---|---|---|---|---|
| Emb. | FIG. | Front and back panels | 1st Elast. layer | 2nd Elast. layer | 3rd Elast. layer | PU foam layer | PE layer |
| [1] | 19A | 1.6 mm (1/16 in.) | 25.4 mm (1 in.) | — | — | 25.4 mm (1 in.) | 6.35 mm (1/4 in.) |
| [2] | 19B | 1.6 mm (1/16 in.) | 25.4 mm (1 in.) | 9.5 mm (3/8 in.) | — | 25.4 mm (1 in.) | — |
| [3] | 19B | 1.6 mm (1/16 in.) | 19 mm (3/4 in.) | 9.5 mm (3/8 in.) | — | 12.7 mm (1/2 in.) | — |
| [4] | 20 | 0.8 mm (1/32 in.) | 29 mm (1.125 in.) | 15.9 mm (5/8 in.) | — | 19 mm (3/4 in.) | 9.5 mm (3/8 in.) |
| [5] | 20 | 0.8 mm (1/32 in.) | 19 mm (3/4 in.) | 9.5 mm (3/8 in.) | — | 19 mm (3/4 in.) | 9.5 mm (3/8 in.) |
| [6] | 20 | 0.8 mm (1/32 in.) | 12.7 mm (1/2 in.) | 12.7 mm (1/2 in.) | — | 25.4 mm (1 in.) | 6.35 mm (1/4 in.) |
| [7] | 20 | 0.8 mm (1/32 in.) | 12.7 mm (1/2 in.) | 9.5 mm (3/8 in.) | — | 12.7 mm (1/2 in.) | 3.2 mm (1/8 in.) |
| [8] | 20 | 1.6 mm (1/16 in.) | 19 mm (3/4 in.) | 12.7 mm (1/2 in.) | — | 12.7 mm (1/2 in.) | 6.35 mm (1/4 in.) |
| [9] | 21A | 1.6 mm (1/16 in.) | 19 mm (3/4 in.) | 12.7 mm (1/2 in.) | 12.7 mm (1/2 in.) | 19 mm (3/4 in.) | — |
| [10] | 21B | 1.6 mm (1/16 in.) | 19 mm (3/4 in.) | — | 12.7 mm (1/2 in.) | 19 mm (3/4 in.) | 9.5 mm (3/8 in.) |
| [11] | 21C | 1.6 mm (1/16 in.) | 19 mm (3/4 in.) | 9.5 mm (3/8 in.) | 12.7 mm (1/2 in.) | 19 mm (3/4 in.) | 6.35 mm (1/4 in.) |
| [12] | 22A | 0.8 mm (1/32 in.) | 9.5 mm (3/8 in.) | 9.5 mm (3/8 in.) | — | — | 6.35 mm (1/4 in.) |
| [13] | 22B | 0.8 mm (1/32 in.) | 9.5 mm (3/8 in.) | 12.7 mm (1/2 in.) | — | — | — |

Referring to the above TABLE 2, for certain figures, multiple alternate embodiments are included, each of which is listed on a separate row under the corresponding figure label. In particular, two rows labeled "FIG. 19B" (see embodiments [2] and [3]) correspond to different embodiments associated with the same arrangement of layers shown in FIG. 19B. Similarly, five rows labeled "FIG. 20" (see embodiments [4]-[8]) correspond to different embodiments associated with the same arrangement of layers shown in FIG. 20. Additionally, the thickness values are presented as examples to illustrate potential configurations and are not intended to be limiting. These values may vary depending on material properties and intended applications (e.g., patient needs). The thickness of each layer is selected provide an optimal balance of strength, flexibility, support, and resilience for the intended application. Each thickness value may be selected from a broader range, such as the broad and sub-ranges described above, or from the following ranges provided in connection with each of embodiments [1]-[13].

The embodiments described in TABLE 2 are associated with different body types, each intended to provide optimal performance and comfort for various users. While TABLE 2 outlined the primary characteristics of each embodiment, TABLE 3 identifies exemplary body types suitable for each embodiment with an accompanying explanation. However, it should be understood that many people exhibit a combination of body types rather than fitting strictly into one category. Additionally, different support pads may be appropriate for the same patient at different stages of recovery (e.g., pre-op, post-surgery).

TABLE 3

| Correlation Between Embodiments and Corresponding Body Types | | | | |
|---|---|---|---|---|
| Emb. | FIG. | Pad | Body type(s) | Sub-class |
| [1] | 19A | 1900 | Ectomorph | Muscular |
| [2] | 19B | 1910 | Ectomorph | Muscular |
| [3] | 19B | 1910 | Ectomorph | Slim |
| [4] | 20 | 2000 | Mesomorph | Muscular |
| [5] | 20 | 2000 | Endomorph | Portly |
| [6] | 20 | 2000 | Mesomorph | Average-stocky |
| [7] | 20 | 2000 | Ectomorph | Thin-muscular |
| [8] | 20 | 2000 | Mesomorph | Average |
| [9] | 21A | 2100 | Endomorph | Muscular |
| [10] | 21B | 2110 | Endomorph | Muscular |
| [11] | 21C | 2120 | Endomorph | Muscular |
| [12] | 22A | 2200 | Endomorph | Average |
| [13] | 22B | 2210 | Endomorph | Average |

In regards to the above TABLES 2 and 3, Embodiments [1]-[2], which correspond to FIG. 19A and FIG. 19B, respectively, are particularly suited for users with a more muscular ectomorph body type. This class of individuals has a lean, but toned physique, and thus requires less rebound resilience as compared with other embodiments. In general, bulkier body frames (e.g., mesomorph and endomorph) require more effort transitioning from a bent-over position (~90 degrees) to an upright position (~180 degrees). The ectomorph class generally requires less effort due to their leaner composition. However, a muscular ectomorph will likely undergo strenuous physiotherapy to regain their initial physique, thereby requiring some rebound assistance. Accordingly, the support pads require either polyethylene layer 1336 (FIG. 19A, support pad 1900) or second elastomer layer 1338 (FIG. 19B, support pad 1910).

Embodiment [3], which also corresponds to FIG. 19B, is particularly suited for a slim, less-toned ectomorph body type. Since this class of individual does not need to regain a muscular physique, less rebound resilience is needed in support pad 1910 of this embodiment. The second elastomer layer 1338 merely needs to provide rebound resilience to assist the user with day-to-day activities and a less strenuous physiotherapy regimen. Similarly, it is expected that a slim ectomorph is not very physically active and thus requires less polyurethane foam against injury protection.

Embodiments [4]-[6] and 8, which all correspond to FIG. 20, are particularly suited for users with the bulkier mesomorph body type or the average to overweight (portly) endomorph body type. These classes of individuals require additional rebound resilience. Embodiment [4] is particularly suited for a muscular mesomorph, who will likely undergo strenuous physiotherapy to regain their initial physique, thereby requiring additional rebound resilience in support pad 2000 as compared with other embodiments.

Embodiment [5] is particularly suited for an overweight (portly) endomorph body type. This class of individual may require extra rebound assistance for day-to-day activities, but less than compared with the muscular mesomorph of Embodiment [4]. Accordingly, the support pads 2000 of Embodiment [5] may require additional rebound resilience as compared with some of the other embodiments.

Embodiments [6] and [8] are particularly suited for an average-to-stocky mesomorph body type and an average mesomorph body type, respectively. These classes of individuals will likely undergo a less strenuous physiotherapy regimen as compared to the muscular mesomorph of embodiment [4]. Accordingly, the support pads 2000 of Embodiments [6] and [8] may require less rebound resilience as compared with other embodiments.

Embodiment [7], which also corresponds to FIG. 20, is particularly suited for a slim-muscular ectomorph body type. (This class of individual is less muscular than the muscular ectomorph of Embodiment [1].) Due to the individual's slim, but toned physique, support pad 2000 requires less rebound resilience as compared with Embodiments [4]-[6]. However, this body type has less initial musculature as compared with Embodiments [1]-[2], and thus requires both a polyethylene layer 1336 and a second elastomer layer 1338. In another embodiment, the support pad (2000) may be configured with thicker layer comprising polyethylene layer 1336 to provide rebound assistance or second elastomer layer 1338 to provide rebound assistance, but not both.

Embodiments [9]-[11], which correspond to FIGS. 21A-21C, respectively, are particularly suited for a muscular endomorph body type. These classes of individuals will likely undergo a strenuous physiotherapy regimen. However, a muscular endomorph might retain more muscle mass and strength than someone with a different body type. Also, the strenuous physiotherapy regimen is made more difficult with additional resilient materials (e.g., having both polyethylene layer (1336) and second elastomer layer (1338)). Accordingly, the support pads 2100-2120 of these embodiments may require less rebound resilience as compared with other embodiments. Additional cushioning support is also desirable in view of the strenuous physiotherapy regimen.

Embodiments [12]-[13], which correspond to FIGS. 22A-22B, respectively, are particularly suited for an average endomorph body type (i.e., not muscular, but not portly). This class of individuals will likely undergo a moderate physiotherapy regimen and so require moderate rebound assistance for day-to-day activities. Accordingly, the support pads 2200-2210 require relatively less rebound resilience as compared with some of the other embodiments.

While specific embodiments have been described as particularly suited for particular body types or sub-classes, this classification is not intended to be limiting. Individuals with borderline or intermediate body types may find that multiple embodiments are equally or sufficiently effective. Furthermore, the features described in the embodiments can be adapted or modified to better suit users with various body type variations.

As described in conjunction with the figures, one or more of the embodiments of present disclosure are directed to a ventral hernia binder having a custom-made support pad insert. More specifically, an abdominal hernia binder/belt, with support pad to create gap between the surgery area or an area with weakened musculature and a binder/belt. The binder or belt may have an airbag or inflatable insert or support pad in the region of the hernia. The binder or belt may have an airbag or inflatable insert, or support or structural bands in the lumbar area to provide back support. The binder or belt may also include one or more pouches or tabs to hold elements of a TENS device in place.

As shown in FIGS. 1-12, embodiments of a hernia binder apparatus of the present disclosure may comprise a binder that extends around the torso of a patient. The exact specifications, materials used, and method of use of the hernia binder may vary upon manufacturing. The binder material is to be constructed from a fabric that is strong and supportive, while providing flex and a minimal level of extensibility in line with other binders 404 known in the field.

The binder may be secured by one or more different types of fasteners. In one embodiment, a hook and mesh fastener may be used, otherwise known as Velcro®. In other embodiments, buckles and belts may also be employed. Clip fasteners, as shown in FIGS. 4 and 5 may secure the binder in place. Fasteners such as buckles, belts and clips may be used alone or in conjunction with known hook and loop fasteners.

In some embodiments, the binder and/or support pad of the present disclosure may include components to allow for transcutaneous electrical nerve stimulation (TENS) treatment of the hernia site. These components may include TENS electrical unit electrode pads, wiring, controller hardware, batteries and other standard TENS unit components. The ability to provide TENS treatment can assist the patient in the healing of the hernia site.

The binder includes one or more pouches or pockets to holes the various additional features in place. The additional features may include a hernia custom insert 302, an air bag/bladder 1004 and TENS equipment. The pouches or pockets may also feature means of holding wires or tubes in place. Such means may be poppers, buttons, and hooks, and include loops or sleeves of fabric.

The custom-made support pad 302 is to be made according to methods, and materials, known in the field, including molding and 3D printing methods. The area of weakens tissue, often corresponding to the area of implanted mesh 202, measured by techniques known in the field including but not limited to laser 3D imagery, plaster casting, or MRI to determine the exact shape and hernia depression over the mesh. Once support pad 302 is placed inside the binder, it helps keep the mesh from distending while performing strenuous activities that wouldn't be done normally.

In accordance with additional embodiments of the present disclosure, the binder may include several other features to support or ease pain in the lumbar region of the body. These may include a pump-up air bladder or somewhat rigid support bands to support the lumbar region. The air bladder or support bands are typically fitted inside a corresponding pocket or pouch in the binder 404.

In accordance with further embodiments of the present disclosure, the binder may include an pump up air bladder or somewhat rigid support bands to support the weakened herniated tissue. The air bladder or support bands are typically fitted inside a corresponding pocket or pouch in the binder 404 to add additional support to the custom-made support pad 302.

In accordance with yet additional embodiments of the present disclosure, the binder may also be specifically adapted to support and retain various equipment associated with the installation of a TENS device. The TENS device being positioned in the lumbar region to relieve back pain.

In some embodiments, the apparatus may include various other support structures, such a groin support.

The binder is easy to wash, the support pad may be flexible or solid and is also washable, can be made to fit different type and sizes of ventral hernias, as well as work with different binder models. In some embodiments, the flexible binder is not configured to provide considerable provide hernia support; rather, such support is provided by the additional features, including, but not limited to, the custom-made multilayered support pads described above.

The following is a list of reference numerals and associated parts as used in this specification and drawings:

| Part | Reference numeral |
|---|---|
| Mesh | 202 |
| 3D measuring device | 204 |
| Custom-made support pad | 302 |
| Abdomen | 304 |
| Mesh | 402 |
| Binder | 404 |
| Second securement means | 406 |
| First securement means | 408 |

-continued

| Part | Reference numeral |
|---|---|
| Pouch (for receiving support pad 302) | 502 |
| Groin support member | 802 |
| Full body compression outfit/suit | 904 |
| Extended binder | 906 |
| Binder | 1002 |
| Air bag/bladder | 1004 |
| Air bag/bladder nozzle | 1006 |
| TENS unit switch | 1102 |
| TENS unit pads | 1104 |
| Support bands | 1202 |
| Multilayered support pad | 1300 |
| Outer cover | 1310 |
| Front (or first) panel | 1312 |
| Back (or second) panel | 1314 |
| Zipper assembly | 1315 |
| Continuous side panel, Fixed side panel, or Seamed flange(s) | 1316 |
| First and second seamed flanges | 1316a, 1316b |
| First (or front) zipper flange | 1317 |
| First (or front) set of interlocking teeth | 1318 |
| Second (or back) zipper flange | 1319 |
| Second (or back) set of interlocking teeth | 1320 |
| Seam | 1322 |
| Inner cavity (of Cover) | 1324 |
| Plurality of intermediate (or core) layers | 1330 |
| High-density foam layer (e.g., Polyurethane-based HD foam) | 1332 |
| First (compressible) elastomer layer (e.g., Neoprene) | 1334 |
| Polyethylene layer (e.g., UHMWPE) | 1336 |
| Second elastomer layer or resilient elastomer layer (e.g., Vulcanized rubber) | 1338 |
| Third elastomer layer or another compressible elastomer layer (e.g., Neoprene) | 1340 |
| Base layer | 1350 |
| Margin portion (of Base layer) | 1352 |
| Multilayered support pad (of FIG. 19A) | 1900 |
| Multilayered support pad (of FIG. 19B) | 1910 |
| Multilayered support pad (of FIG. 20) | 2000 |
| Multilayered support pad (of FIG. 21A) | 2100 |
| Multilayered support pad (of FIG. 21B) | 2110 |
| Multilayered support pad (of FIG. 21C) | 2120 |
| Multilayered support pad (of FIG. 22A) | 2200 |
| Multilayered support pad (of FIG. 22B) | 2210 |
| First end (of zipper assembly 1315) | "A" |
| Second end (of zipper assembly 1315) | "B" |
| Arrow indicating direction of insertion | "C" |

The foregoing descriptions of specific embodiments of the present disclosure have been presented for purposes of illustration and description. They are not intended to be exhaustive or to limit the present disclosure and method of use to the precise forms disclosed. Obviously, many modifications and variations are possible in light of the above teaching. The embodiments described were chosen and described in order to best explain the principles of the present disclosure and its practical application, and to thereby enable others skilled in the art to best utilize the present disclosure and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present disclosure.

The invention claimed is:

1. A ventral hernia binder apparatus, consisting of:

a binder belt having an inner surface and an outer surface; a pouch positioned on said inner surface of said binder belt, said pouch being sized and positioned to correspond to a location of a ventral hernia; and a custom-made hernia support pad configured to be removably integrated within said pouch, the support pad having a multilayered structure consisting of:

an outer cover configured to be insertable into and removable from said pouch, said outer cover including:

a front panel and a back panel, each having a perimeter, each of the front panel and the back panel of the support pad is comprised of an aromatic polyamide, an aliphatic polyamide, or a lignocellulose fiber, or a combination thereof; and one or more side flanges connecting the perimeter of the front panel to the perimeter of the back panel to form an enclosed structure, the enclosed structure defining an interior cavity; and a plurality of intermediate layers arranged in a stacked configuration and having a perimeter, the plurality of intermediate layers configured to be removably positioned in the interior cavity between the front and back panels, said plurality of intermediate layers;

wherein at least two of the intermediate layers are composed of a polymeric material different from the materials of the front and back panels.

2. The ventral hernia binder apparatus of claim 1, wherein the plurality of intermediate layers includes a shock-absorbing high-density foam layer proximate or adjacent to the front panel.

3. The ventral hernia binder apparatus of claim 2, wherein the plurality of intermediate layers further includes a compressible first elastomer layer and a resilient second elastomer layer, wherein the first elastomer layer comprises a foam, without any gel, and is proximate or adjacent to the back panel, and wherein the second elastomer layer is positioned between the high-density foam layer and the first elastomer layer.

4. The ventral hernia binder apparatus of claim 3, wherein the plurality of intermediate layers further includes a polyethylene layer positioned adjacent or proximate to the second elastomer layer.

5. The ventral hernia binder apparatus of claim 4, wherein the plurality of intermediate layers further includes a compressible third elastomer layer comprising a foam rubber, without any gel, and positioned adjacent or proximate to the high-density foam layer.

6. The ventral hernia binder apparatus of claim 3, wherein the plurality of intermediate layers further includes a compressible third elastomer layer comprising a foam rubber, without any gel, and positioned between the high-density foam layer and the second elastomer layer.

7. The ventral hernia binder apparatus of claim 2, wherein the plurality of intermediate layers further includes another shock-absorbing high-density foam layer and a polyethylene layer, wherein the another shock-absorbing high-density foam layer is proximate or adjacent to the back panel, and wherein the polyethylene layer is positioned between the high-density foam layer and the another high-density foam layer.

8. The ventral hernia binder apparatus of claim 7, wherein the plurality of intermediate layers further includes a resilient elastomer layer positioned between the high-density foam layer and the another high-density foam layer.

9. The ventral hernia binder apparatus of claim 2, wherein the plurality of intermediate layers further includes a compressible elastomer layer and a polyethylene layer, wherein the compressible elastomer layer comprises a foam rubber, without any gel, and is proximate or adjacent to the back panel, and wherein the polyethylene layer is positioned between the high-density foam layer and the compressible elastomer layer.

10. The ventral hernia binder apparatus of claim 9, wherein the plurality of intermediate layers further includes another compressible elastomer layer comprising a foam rubber, without any gel, and positioned between the high-density foam layer and the polyethylene layer.

11. The ventral hernia binder apparatus of claim 1, wherein the plurality of intermediate layers includes a compressible elastomer layer comprising a foam rubber, without any gel, proximate or adjacent to the back panel.

12. The ventral hernia binder apparatus of claim 11, wherein the plurality of intermediate layers further includes a resilient elastomer layer.

13. The ventral hernia binder apparatus of claim 12, wherein the plurality of intermediate layers further includes a polyethylene layer proximate or adjacent to the front panel.

14. The ventral hernia binder apparatus of claim 11, wherein the plurality of intermediate layers further includes another compressible elastomer layer comprising a foam rubber, without any gel.

15. The ventral hernia binder apparatus of claim 1, wherein the plurality of intermediate layers includes a shock-absorbing high-density foam layer proximate or adjacent to the back panel.

16. The ventral hernia binder apparatus of claim 15, wherein the plurality of intermediate layers further includes a compressible elastomer layer comprising a foam rubber, without any gel, proximate or adjacent to the high-density foam layer.

17. The ventral hernia binder apparatus of claim 1, wherein the plurality of intermediate layers includes a polyethylene layer.

18. The ventral hernia binder apparatus of claim 1, wherein the support pad further includes a base layer positioned between the plurality of intermediate layers and the back panel, wherein the base layer extends laterally beyond the perimeter of the plurality of intermediate layers to define a peripheral margin.

19. The ventral hernia binder apparatus of claim 1, wherein the interior cavity is accessible via a zipper assembly.

* * * * *